US006451322B1

(12) United States Patent
Rovinski et al.

(10) Patent No.: US 6,451,322 B1
(45) Date of Patent: Sep. 17, 2002

(54) RETROVIRUS LIKE PARTICLES MADE NON INFECTIOUS BY A PLURALITY OF MUTATIONS

(75) Inventors: Benjamin Rovinski, Thornhill; Shi-Xian Cao, Etobicoke; Fei-Long Yao; Roy Persson, both of North York; Michel H. Klein, Willowdale, all of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 09/258,128

(22) Filed: Feb. 26, 1999

Related U.S. Application Data

(63) Continuation of application No. 08/292,967, filed on Aug. 22, 1994, now abandoned.

(51) Int. Cl.[7] .................................. A61K 39/21

(52) U.S. Cl. .............................. 424/208.1; 424/188.1; 536/23.72; 435/69.1; 435/69.7; 435/235.1; 435/320.1

(58) Field of Search ......................... 435/5, 69.1, 69.7, 435/235.1, 236; 424/188.1, 208.1, 192.1, 199.1

(56) References Cited

U.S. PATENT DOCUMENTS 5,352,449 A 10/1994 Beltz et al.

FOREIGN PATENT DOCUMENTS

| | | | |
|---|---|---|---|
| WO | WO 89/05349 | * | 6/1989 |
| WO | WO 91/05860 | | 5/1991 |
| WO | WO 91/05864 | * | 5/1991 |
| WO | WO 91/07425 | | 5/1991 |
| WO | WO 93/20220 | | 10/1993 |
| WO | WO 96/05292 | * | 2/1996 |

OTHER PUBLICATIONS

Wain–Hobson, S., Sonigo, P., Danos, O., Col, S. and Alizon, M. (1985) Cell, 40, 9–17.

Myers, G., Berzofsky, J.A., Rabson, A.B., Smith, T.F. and Wong–Staal, F. (ed.) (1990) Human retroviruses and AIDS. Theoretical Biology and Biophysics, Group T–10. Los Alamos National Laboratory, Los Alamos, N.Mex.

Alizon, M., Sonigo, P., Barre–Sinoussi, F., Chermann, J.C., Tiollais, P., Montagnier, L. and Wain–Hobson, S. (1984) Nature, 312, 757–780.

Min Jou, W., Verhoeyen, M., Devos, R., Saman, E., Fang, R., Huylebroeck, D. and Fiers, W. (1980) Cell, 19, 683–696.

Westhof, E., Altschuh, D., Moras, D., Bloomer, A.C., Mondragon, A., Klug, A. and Van Regenmortel, M.H. (1984) Nature, 311, 123–126.

Trifilieff, E., Dubs, M.C. and Van Regenmortel, M.H.V. (1991) Mol. Immunol., 28, 889–896.

Kieny, M.P. (1990) J. Acquired Immune Deficiency Syndromes, 3, 395–402.

Ulmer, J.B., Donnelly, J.J. and Liu, M.A. (1993) Curr. Opin. Invest. Drugs 2(9), 983–989.

Martin et al, 1993, J. Biol. Chm. 268:2565–2570.

Berman et al, 1990, Nature 345: 622–625.

(List continued on next page.)

*Primary Examiner*—Laurie Scheiner
*Assistant Examiner*—Jeffrey S. Parkin
(74) *Attorney, Agent, or Firm*—Sim & McBurney

(57) ABSTRACT

Non-infectious, retrovirus-like particles contain mutations to reduce gag-dependent RNA-packaging of the gag gene product, eliminate reverse transcriptase activity of the pol gene product, eliminate integrase activity of the pol gene, product and eliminate RNase H activity of the pol gene product through genetic manipulation of the gag and pol genes. The corresponding nucleic acid molecules are described. The non-infectious, retrovirus-like particles have utility in in vivo administration including to humans and in diagnosis.

29 Claims, 12 Drawing Sheets

OTHER PUBLICATIONS

Klein, M. et al; AIDS Research and Human Retroviruses, "Development of a cross–neutralizing HIV–1 pseudovirion–based vaccine", vol. 9. No. Sup 1, Oct. 1993.*

Bowles, et al; Virology, "Site–directed mutagenesis of the P2 region of the Rous Sarcoma Virus gag gene: effects on gag polyproptein processing", vol. 203, No. 1, Aug. 15, 1994, pp. 20–28.*

Sakalian, M. et al; Journal of Virology, "Efficiency and selectivity of RNA packaging by Rous Sarcoma Virus gag deletion mutants", vol. 68, No. 9, Sep. 1994, pp. 5969–5981.*

Zhang, Y. et al; Journal of Virology, "Nucleocapsid protein effects on the specificity of retrovirus RNA encapsidation", vol. 69, No. 9, pp. 5716–5722.*

Coffin, J. 1996, "Retroviridae: The Viruses and Their Replication", in Fields Virology, Third Edition, Fields et al, eds., Lippincott–Raven Publishers, Philadelphia, p. 1770.

Hunter, E., 1994, Sem Virol. 5:71–83.

Karacostas et al, 993, Virol. 193:661–671.

Drelich et al., "Identification of amino acid residues critical for endonuclease and integration activities of HIV–1 IN protein in vitro," Virology, 1992, 188(2):459–68.

Haynes, J., et al., 1991, "Production of immunogenic HIV–1 viruslike particles in stably engineered monkey cell lines", AIDS Res. Human Retrovir. 7(1):17–27.*

Rovinski, B., et al., 1992, "Expression and characterization of genetically engineered human immunodeficiency virus–like particles containing modified envelope glycoproteins: implications for development of a cross–protective AIDS vaccine", J. Virol. 66(7):4003–4012.*

Aldovini, A. and R. Young, 1990, "Mutations of RNA and protein sequences involved in human immunodeficiency virus type 1 packaging result in production of noninfectious virus", J. Virol. 64(5):1920–1926.*

Gorelick, R., et al., 1993, "The two zinc fingers in the human immunodeficiency virus type 1 nucleocapsid protein are not functionally equivalent", J. Virol. 67(7):4027–4036.*

Martin, J., et al., 1993, "Biochemical analysis of human immunodeficiency virus–1 reverse transcriptase containing a mutation at position lysine 263", J. Biol. Chem. 268(4):2565–2570.*

Tisdale, M., et al., 1991, "Mutations within the RNase H domain of human immunodeficiency virus type 1 reverse transcriptase abolish virus infectivity", J. Gen. Virol. 72:59–66.*

Shaharabany, M., et al., "Expression and mutational analysis of the reverse transcriptase of the lentivirus equine infectious anemia virus", Biochem. Biophys. Res. Comm. 196(2):914–920.*

Edelman, R. and C. Tacket, 1990, "Adjuvants", Intern. Rev. Immunol. 7:51–66.*

* cited by examiner

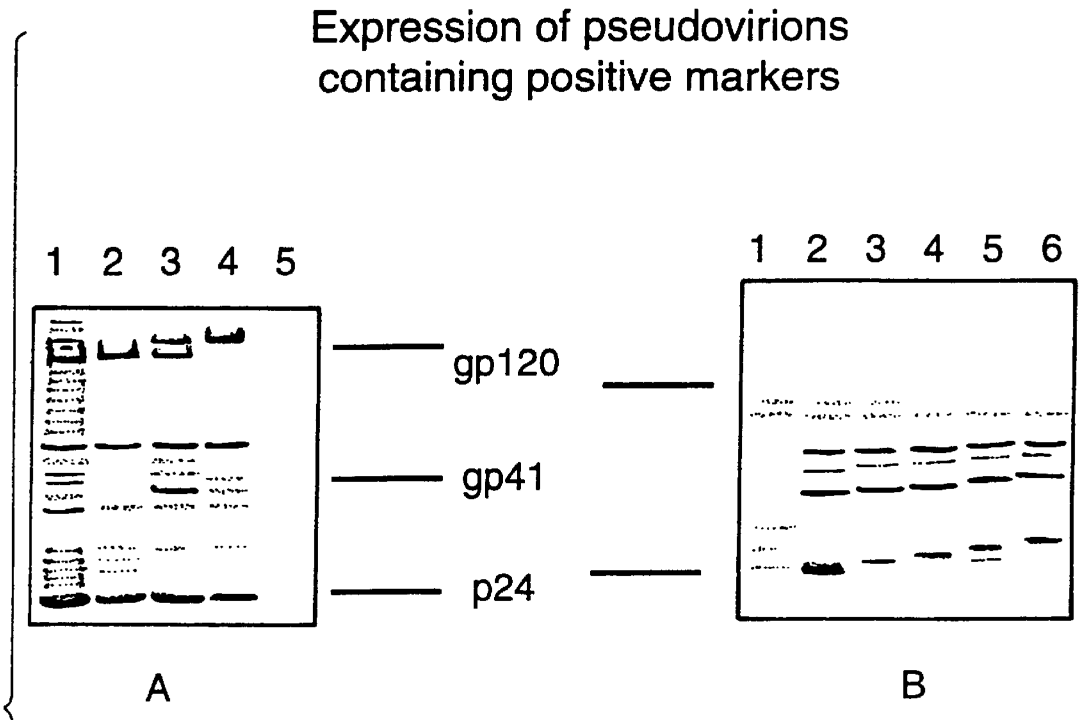

A. Western blot analysis of pseudovirions containing the human mHA2 epitope (lanes 1 and 2); "wild type" virions (lane 3); pseudovirions containing unprocessed gp160 (lane 4); and pelleted material from mock-transfected Vero cells (lane 5).
B. Western blot analysis of"wild-type pseudovirions (lane 2), and pseudovirions containing either one (lane 3), two (lane 4), three (lane 5), or four (lane 6) copies of the TMV epitope.

FIG.11

RETROVIRUS LIKE PARTICLES MADE NON INFECTIOUS BY A PLURALITY OF MUTATIONS

REFERENCE TO RELATED APPLICATION

This application is a continuation of U.S. patent application Ser. No. 08/292,967 filed Aug. 22, 1994 (now abandoned).

FIELD OF THE INVENTION

The present invention relates to the field of immunology and is particularly concerned with retrovirus-like particles (sometimes termed pseudovirions), made non-infectious by a plurality of mutations.

BACKGROUND OF THE INVENTION

Human immunodeficiency virus is a human retrovirus and is the etiological agent of acquired immunodeficiency syndrome (AIDS). Since AIDS was first reported in the US in 1981, more than 194,000 people have died of AIDS and over 330,000 cases of HIV infection have been reported in the US alone. Worldwide, it is estimated that more than 17 million people have been infected with HIV.

More than 100 AIDS-related medicines are in human clinical trials or awaiting FDA approval but there is currently no cure for the disease.

There is, therefore, a clear need for immunogenic preparations useful as vaccine candidates, as antigens in diagnostic assays and kits and for the generation of immunological reagents for diagnosis of HIV and other retroviral disease and infection.

Particular prior art immunogenic preparations include non-infectious, non-replicating HIV-like particles. Thus PCT applications WO 93/20220 published Oct. 14, 1993 and WO 91/05860 published May 2, 1990 (Whitehead Institute for Biomedical Research), teach constructs comprising HIV genomes having an alteration in a nucleotide sequence which is critical for genomic RNA packaging, and the production of non-infectious immunogenic HIV particles produced by expression of these constructs in mammalian cells.

PCT application WO 91/07425 published May 30, 1991 (Oncogen Limited Partnership) teaches non-replicating retroviral particles produced by co-expression of mature retroviral core and envelope structural proteins, such that the expressed retroviral proteins assemble into budding retroviral particles. A particular non-replicating HIV-1 like particle was made by coinfecting mammalian host cells with a recombinant vaccinia virus carrying the HIV-1 gag and protease genes and a recombinant vaccinia virus carrying the HIV-1 env gene.

In published PCT application WO 91/05864 in the name of the assignee hereof (which is incorporated herein by reference thereto), there are described particular non-infectious, non-replicating retrovirus-like particles containing at least gag, pol and env proteins in their natural conformation and encoded by a modified retroviral genome deficient in long terminal repeats and containing gag, pol and env genes in their natural genomic arrangement.

Virions of HIV comprise two copies of the single-stranded RNA genome enclosed within a capsid. After penetration into a susceptible host cell, the HIV genome is copied by the viral reverse transcriptase into single-stranded DNA that is thought to be translocated into the nucleus, wherein a cellular DNA polymerase synthesizes the second DNA strand. The double-stranded copy is then integrated, at random, into one of the host chromosomes, resulting in a duplication of a region of the viral genome at the extremities of the genome. The long-terminal repeat (LTR) of the integrated provirus is recognized by a cellular RNA polymerase and the transcribed RNA is translated to give rise to viral proteins. The RNA transcripts can also be packaged into new virions that leave the cell by a process of budding.

The HIV genome encodes at least nine different proteins. The three major genes, gag, pol and env are common to all retroviruses and encode virion proteins.

The differential expression of these genes is achieved through a complex pattern of processing of the primary precursor transcript. Only the GAG and POL proteins are produced from the unspliced mRNA corresponding to the genomic RNA of the virion. The ENV protein is translated from a mRNA species that has undergone a single splicing event to delete the gag and pol coding sequences, and other proteins are produced from mRNA species that are spliced several times. The general structure of HIV is reviewed by Kieny et al (ref. 8).

Thus, it may be advantageous under particular circumstances to produce. retrovirus-like particles (and in particular HIV-like particles) by mutating other portions of the HIV genome contributing to infectivity and replication of the virus. Such modifications may be modifications of the gag and pol gene products.

There is currently no vaccine nor effective treatment for AIDS. Heat-inactivated anti-HIV antiserum obtained from HIV-infected people and inactivated HIV are currently commercially available as components of many diagnostic methods. For safety, ease of handling, shipping, storage and use, it may be preferable to replace such antigen and heat-inactivated antisera by non-infectious HIV-like particles and antisera generated by immunization with non-infectious HIV-like particles as described above and particularly in WO 91/05864. Furthermore, antisera generated by immunization with these non-infectious HIV particles do not require heat inactivation to remove infectious HIV. The HIV-like particles described in WO 91/05864 are entirely deficient in replication and infection. However, because of the seriousness of HIV infection, it may be desirable under certain circumstances to provide retrovirus-like particles deficient in a plurality of elements required for infectivity and/or replication of HIV but dispensible for virus-like particle formation. Furthermore, since prior art HIV-like particles contain many of the HIV proteins in substantially their natural conformations, a host immunized therewith may mount an immune response immunologically indistinguishable from infection by HIV and it may be desirable to be able to distinguish between inactivated HIV and non-infectious, non-replicating HIV particles and antisera generated by virulent HIV and non-infectious, non-replicating HIV-like particles. Thus, in the development of AIDS vaccine candidates, immunogenic preparations and diagnostic methods and kits, it would be useful to provide an HIV-like particle deficient in a plurality of elements required for infectivity and/or replication and optionally immunologically or otherwise distinguishable from virulent HIV.

SUMMARY OF THE INVENTION

The present invention is directed towards the provision of retrovirus-like particles made non-infectious by a plurality of mutations.

Accordingly, in one aspect of the invention there is provided a non-infectious immunogenic, retrovirus-like particle comprising, in an assembly, gag, pol and env gene products, wherein at least one modification has been made to the pol and/or gag gene product, to effect at least one of the following (a) reduce gag-dependent RNA packaging of the gag gene product;

(b) substantially eliminate reverse transcriptase activity of the pol gene product;

(c) substantially eliminate integrase activity of the pol gene product; and (d) substantially eliminate RNase H activity of the pol gene product.

The reduction in gag dependent RNA packaging may be effected by replacing or deleting at least one amino acid residue contributing to gag-dependent RNA packaging in the gag gene product. In an illustrative embodiment, the at least one amino acid may be contained within amino acids $Cys^{392}$ to $Cys^{395}$ of the gag gene product of HIV-1 LAI isolate or the corresponding region of other retroviral gag gene products and $Cys^{392}$ and/or $Cys^{395}$ or both cysteines may be replaced by serine residues.

In one specific illustrative embodiment of the invention, the substantial elimination of reverse transcriptase activity of the pol gene product may be effected by deletion of at least a portion thereof contributing to reverse transcriptase activity. The at least a portion of the pol gene product may be contained between amino acids $Pro^{168}$ and $Leu^{727}$ of the pol gene product of HIV-1 LAI isolate or the corresponding region of other retroviral pol gene products. The substantial elimination of integrase activity of the pol gene product may be effected by deletion of at least a portion thereof contributing to integrase activity and the at least a portion of the pol gene product may be contained between amino acids $Phe^{728}$ and $Asp^{1016}$ of the pol gene product of HIV-LAI isolate or the corresponding region of other retroviral pol gene products.

The substantial elimination of RNase H activity of the pol gene product may be effected by deletion of at least a portion thereof contributing to RNase H activity.

In a particular embodiment of this aspect of the invention substantial elimination of reverse transcriptase, integrase and RNase H activities may be simultaneously effected by deleting a portion of the pol gene product corresponding to amino acids $Pro^{192}$ to $Trp^{835}$ of HIV-1 LAI isolate, or the corresponding region of other retroviral pol gene products.

In a further aspect of the invention, the non-infectious retrovirus-like particles of the invention may additionally comprise at least one non-retroviral antigenic marker. The incorporation of antigenic markers into non-infectious retrovirus-like particles is described in our copending U.S. patent application Ser. No. 08/290,105 filed Aug. 15, 1994, the disclosure of which is incorporated herein by reference. The at least one antigenic marker may be contained within the gag gene product to form a hybrid gag gene product having the particle-forming characteristics of unmodified gag gene product. In a particular embodiment, the at least one antigenic marker may be inserted into an insertion site of the gag gene product at an antigenically-active insertion site and the insertion site may be located between amino acid residues 210 and 211 of the gag gene product of the HIV-1 LAI isolate or the corresponding location of other retroviral gag gene products. The at least one antigenic marker may comprise from 1 to 4 tandem copies of the amino acid sequence AFDTRNRIIEVEN (SEQ ID NO: 1) or a portion, variation or mutant thereof capable of eliciting antibodies that recognize the sequence AFDTRNRIIEVEN.

The marker sequence also may be provided by deleting or preventing production of an amino acid sequence that corresponds to an epitope of a retroviral protein. Such epitope may comprise the immunodominant epitope of gp41, which provides endogenous anchoring function. When such endogenous anchoring function is removed in this way, the anchoring function is provided by a different antigenic anchor sequence.

In a further particular embodiment of this aspect of the invention, the env gene product of the retrovirus-like particles as provided herein may be a modified env gene product in which endogenous anchoring function has been replaced by a different antigenic anchor sequence opertively connected to the env gene product to anchor the env gene product to the retrovirus-like particle and the anchor sequence may be inserted into an insertion site of the env gene product adjacent to and upstream of functional cleavage sites of the env gene product. The insertion site may be located between amino acid residues 507 and 508 of the env gene product of the HIV-1 LAI isolate or the corresponding location of other retroviral env gene products. The anchor sequence may include an amino acid sequence WILWISFAISCFLLCVVLLGFIMW (SEQ ID NO: 2) or a portion, variation or mutant thereof capable of eliciting antibodies that recognize the sequence WILWISFAISCFLLCVV LLGFIMW.

In yet another embodiment, the anchor sequence may include an amino acid sequence STVASSLALAIMIAGLSFWMCSNG SLQ (SEQ ID NO: 3) or a portion, variation or mutant thereof capable of eliciting antibodies that recognize the sequence STVASSLALAIMIAGLSFWMCSNGSLQ.

In another embodiment, the anchor sequence may include an amino acid sequence WILWISFAISCFLLCVVCWGSSCG PAKKATLGATFAFDSKEEWCREKKEQWE (SEQ ID NO: 4) or a portion, variation or mutant thereof capable of eliciting antibodies that recognize the sequence WILWISFAISCFLLCVVCWGSSCGPAKKATLGATFAFDSKEEWCREKKEQWE.

The retrovirus-like particle generally is a human retrovirus-like particle, particularly derived from HIV-1, HIV-2, HTLV-1 or HTLV-2. Specifically, the human retrovirus may be HIV-1 and the env gene product may be an LAI env gene product, an MN env gene product, an env gene product from a primary HIV-1 isolate, or an env gene product antigenically equivalent thereto.

The present invention also includes nucleic acid molecules encoding the non-infectious, retrovirus-like particles of the invention. Accordingly, in another aspect of the invention, there is provided a nucleic acid molecule encoding a non-infectious, immunogenic, retrovirus-like particle, comprising a modified retroviral genome deficient in long terminal repeats and containing gag, pol and env genes in their natural genomic arrangement and means for expression operatively connected to the modified retroviral genome for production of gene products in cells to produce non-infectious, immunogenic, retrovirus-like particles comprising an assembly of gag, pol and env gene products, wherein at least one codon in the gag or pol gene has been mutated to effect at least one of the following:

(a) reduce gag-dependent RNA packaging activity of the gag gene product;

(b) substantially eliminate reverse transcriptase activity of the pol gene product;

(c) substantially eliminate integrase activity of the pol gene product; and (d) substantially eliminate RNase H activity of the pol gene product. The nucleic acid molecule may comprise a DNA molecule containing the characteristic genetic elements present in a SacI 678 to XhoI 8944 fragment of the genome of the HIV-1 LAI isolate. The modified genome also may be deficient in primer binding site and/or an RNA packaging signal.

The reduction of gag-dependent RNA packaging may be effected by mutagenesis of a region thereof encoding at least one amino acid contained with a region of the gag gene product corresponding to $Cys^{392}$ to $CyS^{395}$ of the HIV-1 LAI isolate, or the corresponding region of other retroviral gene products, and $Cys^{392}$ and/or $Cys^{395}$ or both cysteines may be replaced by serine residues.

In one specific illustrative embodiment of the invention, the substantial elimination of reverse transcriptase activity of the pol gene product may be effected by deletion of at least a part of the pol gene encoding reverse transcriptase and the at least a part of the pol gene deleted may be contained between nucleotides 2586 and 4265 of the pol gene of HIV-1 isolate LAI or the corresponding region of other retroviral pol genes.

In an additional aspect, the substantial elimination of integrase activity of the pol gene product may be effected by deletion of at least a part of the pol gene encoding integrase and in an illustrative embodiment the at least a part of the pol gene deleted may be contained between nucleotides 4266 and 5129 of the pol gene of HIV-1 isolate LAI or the corresponding region of other retroviral pol genes.

The substantial elimination of RNase H activity of the pol gene product may be effected by deletion of at least a part of the pol gene encoding RNase H.

In a further aspect of the invention, there is provided modified retroviral genomes of the invention including a segment encoding at least one antigenic marker.

In one specific illustrative embodiment of this aspect of the invention, the sequence encoding the at least one antigenic marker is inserted into the gag gene at an antigenically active insertion site and specifically at the PstI site at nucleotide 1415 of the gag gene of HIV-1 LAI isolate or the corresponding location of other retroviral gag genes. One specific segment comprises from 1 to 4 copies of a DNA sequence selected from the group consisting of:

(a) 5' GCATTCGACACTAGAAATAGAATAATA-GAAGTTGAAAAT 3'; (SEQ ID NO: 5);

(b) 3' CGTAAGCTGTGATCTTTATCTTAT-TATCTTCAACTTTTA 5'; (SEQ ID NO: 6); and (c) DNA sequences that hybridize with (a) or (b) under stringent conditions, particularly sequences that have at least about 90% sequence identity with the sequence of (a) or (b).

A variety of hybridization conditions may be employed to achieve varying degrees of selectivity of hybridization. For a high degree of selectivity, stringent conditions are used to form duplexes, such as low salt and/or high temperature conditions, such as provided by 0.02 M to 0.15 M NaCl at temperatures of between about 50° C. to 70° C. For some applications, less stringent hybridization conditions may be required such as 0.15 M to 0.9 M salt, at temperatures ranging from between about 20° C. to 55° C. Hybridization conditions can also be rendered more stringent by the addition of increasing amounts of formamide, to destabilize the hybrid duplex.

In a yet further embodiment of the present invention, there is provided a nucleic acid molecule encoding a non-infectious retrovirus-like particle of the invention, comprising a modified retroviral genome deficient in long terminal repeats and containing gag, pol and env genes in their natural genomic arrangement with the env gene being modified to provide therein a segment encoding an antigenic anchor sequence to anchor the env gene product to the retrovirus-like particle, whereby the modified env gene encodes a modified env gene product in which endogenous anchoring function of env has been replaced by the antigenic anchor sequence.

In one specific illustrative embodiment of this aspect of the invention, the segment encoding the antigenic marker sequence is inserted into the env gene, specifically between nucleotide 7777 and 7778 of the env gene of the HIV-1 LAI isolate or the corresponding location of other retroviral env genes. One specific segment encoding the anchor sequence includes a DNA sequence selected from the group consisting of:

(a) 5' TGGATCCTGTGGATTCCTTTGCCATAT-CATGCTTTTTGCTTTG TGTTGTTTTGCTGGGGT-TCATCATGTGG 3'; (SEQ ID NO: 7);

(b) 3' ACCTAGGACACCTAAAGGAAACGGTAT-AGTACGAAAAACGAAAC ACAACAAAACGAC-CCCAAGTAGTACACC 5'; (SEQ ID NO: 8); and (c) DNA sequences that hybridize with (a) or (b) under stringent conditions, particularly sequences that have at least about 90% sequence identity with the sequences of (a) or (b).

Another specific segment encoding the anchor sequence includes a DNA sequence selected from the group consisting of:

(a) 5' TCAACAGTGGCAAGTTCCCTAGCACTG-GCAATCATGATAGC TGGTCTATCTTTTTGGAT-GTGTTCCAATGGGTCATTGCAG 3'; (SEQ ID NO: 9)

(b) 3' AGTTGTCACCGTTCAAGGGATCGTGAC-CGTTAGTACTATCGA CCAGATAGAAAAACCTA-CACAAGGTTACCCAGTAACGTC 5'; and (SEQ ID NO: 10); and (c) DNA sequences that hybridize with (a) or (b) under stringent conditions, particularly sequences that have at least about 90% sequence identity with the sequences of (a) or (b). Another specific segment encoding the anchor sequence is selected from the group consisting of:

(a) 5' TGGATCCTGTGGATTTCCTTTGCCATAT-CATGCTTTTTGCTT TGTGTTGTTTGCTGGGdT-TCATCATGTGGGCCTGCCAAAAAGGCAACATT AGGTGCAACATTTGCATTTGATAGTAAA-GAAGAGTGGTGCAGAGAGAAAA AAGAG-CAGTGGGAA 3'; (SEQ ID NO: 11);

(b) 3' ACCTAGGACACCTAAAGGAAACGGTAT-AGTACGAAAAACGAA ACACAACAAACGAC-CCCAAGTAGTACACCCGGACGGTTTTTC-CGTTGTAA TCCACGTTGTAAACGTAAACTAT-CATTTCTTCTCACCACGTCTCTCTTTT TTCTCGTCACCCTT 5'; and (SEQ ID NO: 12); and (c) DNA sequences that hybridize with (a) or (b) under stringent conditions, particularly sequences that have at least about 90% sequence identity with the sequence of (a) or (b).

The present invention further includes, in an additional aspect, an immunogenic composition capable of eliciting a retroviral specific immune response, comprising the retrovirus-like particles or nucleic acid molecule provided herein, and a carrier therefor. Such composition may be formulated for mucosal or parenteral administration, by oral, anal, vaginal or intranasal routes. The immunogenic composition may comprise at least one other immunogenic or immunostimulating material, specifically an adjuvant, such as aluminum phosphate, aluminum hydroxide, Freund's incomplete adjuvant or QS21.

In a further aspect, the present invention includes a method of immunizing a host to produce a retroviral specific immune response, comprising administering to the host an immunoeffective amount of the immunogenic composition provided herein.

The present invention also includes diagnostic procedures and kits. utilizing those materials. Specifically, in another aspect of the invention, there is provided a method of determining the presence of antibodies specifically reacting with retroviral antigens in a sample, comprising the steps of (a) contacting the sample with the non-infectious retrovirus-like particle provided herein to produce complexes comprising the non-infectious retrovirus-like particles and any said antibodies present in the sample specifically reactive therewith; and (b) determining production of the complexes.

In an additional aspect of the invention, there is provided a method of determining the presence of retroviral antigens in a sample, comprising the steps of (a) immunizing a host with the immunogenic composition provided herein to produce retroviral antigen-specific antibodies; (b) contacting the sample with the retroviral antigen-specific antibodies to produce complexes comprising any retrovirus antigens in the sample and retroviral antigen-specific antibodies; and (c) determining production of the complexes.

A further aspect of the invention provides a diagnostic kit for detecting the presence of retroviral antigens in a sample comprising (a) at least one such retroviral antigen-specific antibody provided herein; (b) means for contacting the at least one antibody with the sample to produce a complex comprising any retroviral antigens in the sample and the retroviral antigen-specific antibodies; and (c) means for determining production of the complex.

Advantages of the present invention include:

an immunogenic retrovirus-like particle comprising gag, pol and env gene products in their natural conformations rendered non-infectious and non-replicating by a plurality of mutations; and an immunogenic retrovirus-like particle immunologically distinguishable from a virulent retrovirus.

BRIEF DESCRIPTION OF THE DRAWINGS

FIG. 11 shows an immunoblot analysis of antigenically marked retrovirus-like particles (pseudovirions)

GENERAL DESCRIPTION OF INVENTION

It is clearly apparent to one skilled in the art, that the various embodiments of the present invention have many applications in the fields of vaccination, diagnosis, treatment of HIV infections, and the generation of immunological reagents. A further non-limiting discussion of such uses is further presented below.

Figure 1:
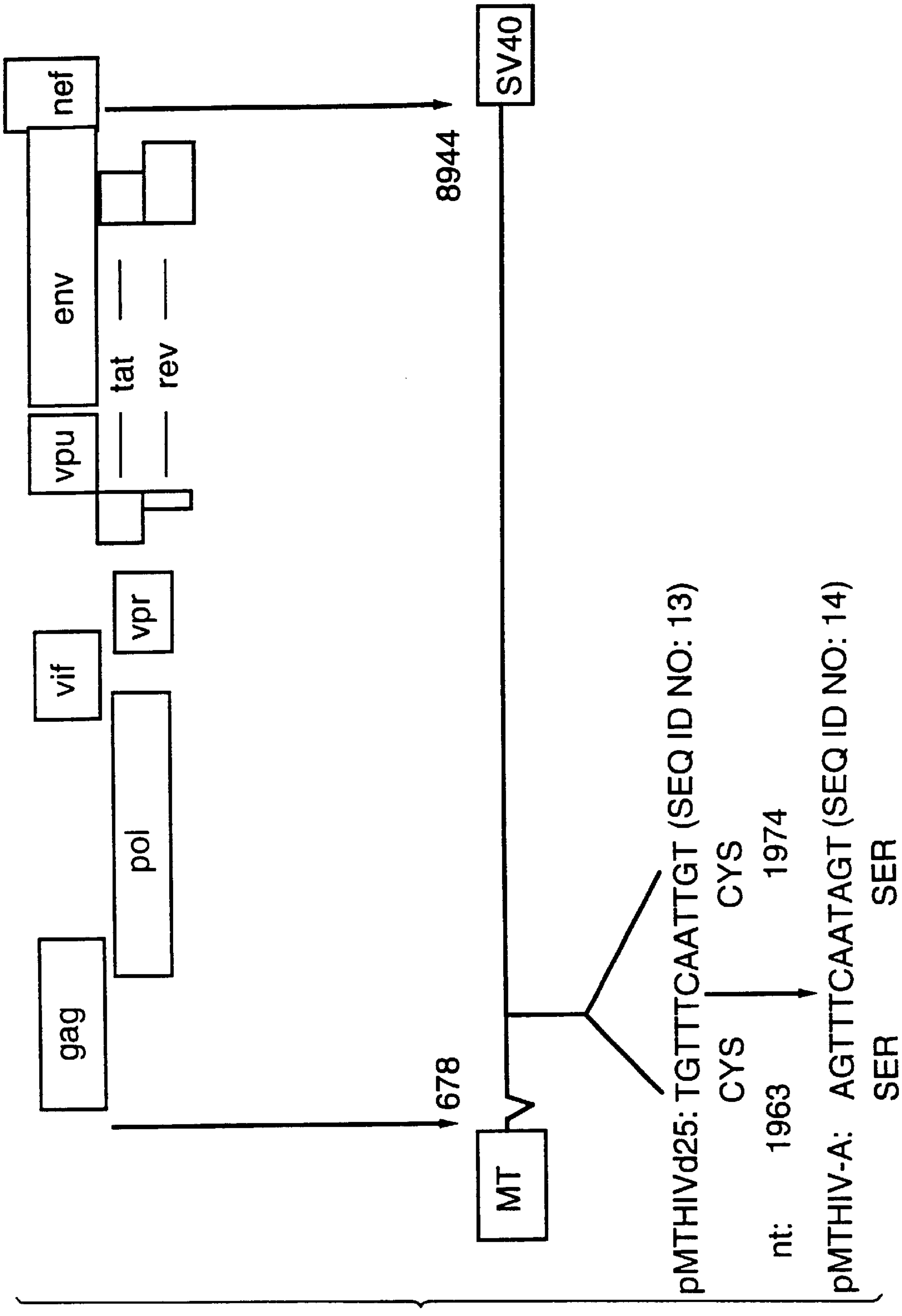
FIG. 1 shows a construction scheme of a plasmid (pMTHIV-A) encoding a retrovirus-like particle having a modification to the gag gene product in accordance with one embodiment of the invention.
Figure 2:
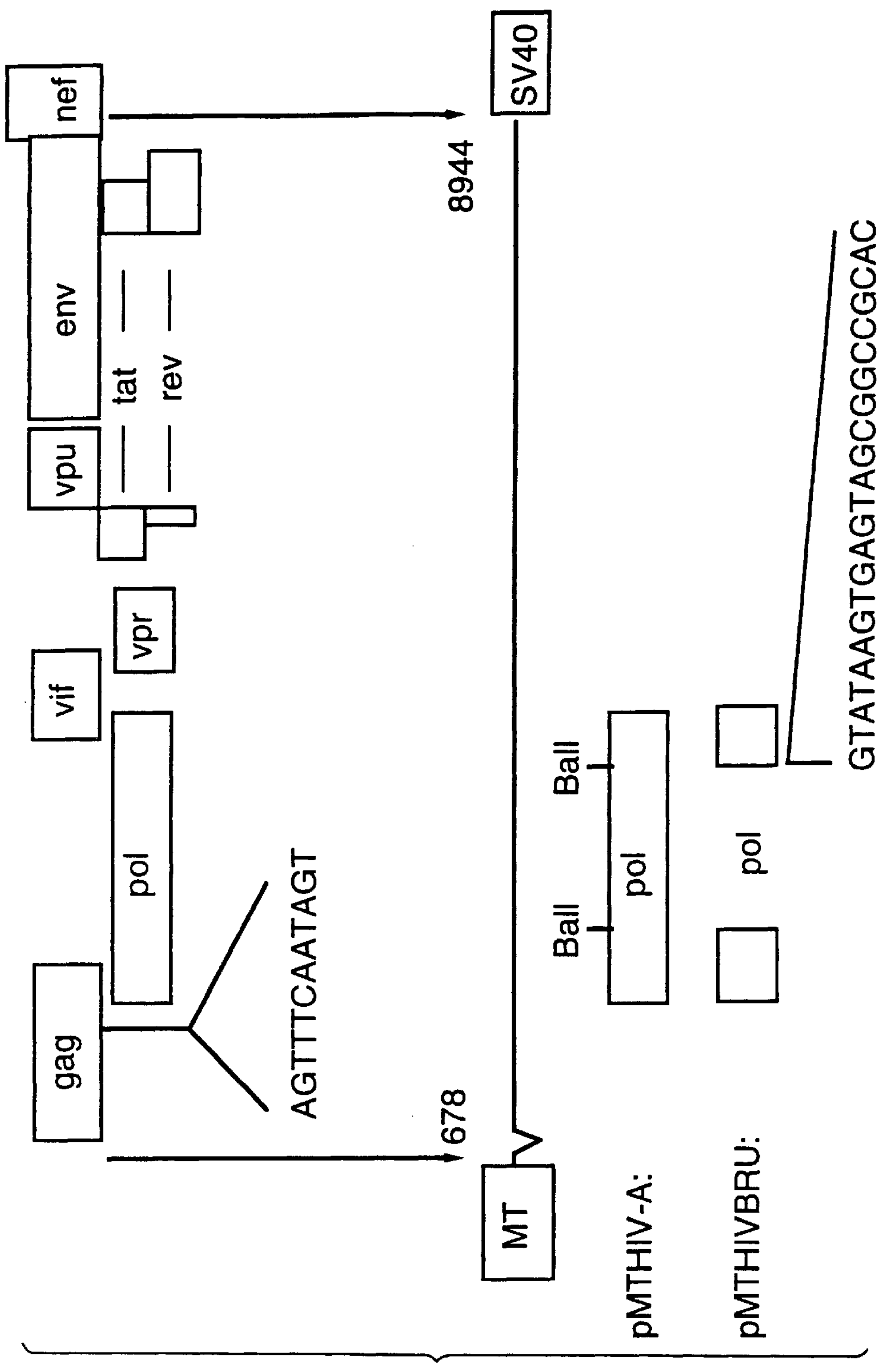
FIG. 2 shows a construction scheme of a plasmid (pMTHIVBRU) encoding a retrovirus-like particle having a modificaiton to both the gag and pol gene products in accordance with a further embodiment of the invention.

Referring to FIGS. 1 and 2, there is illustrated the construction of a vector pMTHIVBRU (ATCC designation 75852) containing a modified retroviral genome deficient in long terminal repeats, primer binding site and an RNA packaging sequence, and containing gag, pol and env genes in their natural genomic arrangement. The pol gene of pMTHIVBRU has been modified by deletion of a portion thereof to substantially remove the reverse transcriptase and integrase activities thereof. Furthermore, in this particular illustrated embodiment of the invention, an oligonucleotide has been inserted within the deleted pol gene to introduce three stop codons in three different reading frames to prevent remaining sequences of integrase from being translated. The gag gene of pMTHIVBRU has also been modified to replace the two cysteine residues ($CyS^{392}$ and $Cys^{395}$) in the first Cys-His box by serines.

Thus, plasmid pMTHIVBRU encodes an HIV-like particle deficient in a plurality of elements required for infectivity and/or replication of HIV but dispensible for virus-like particle production.

Figure 3:
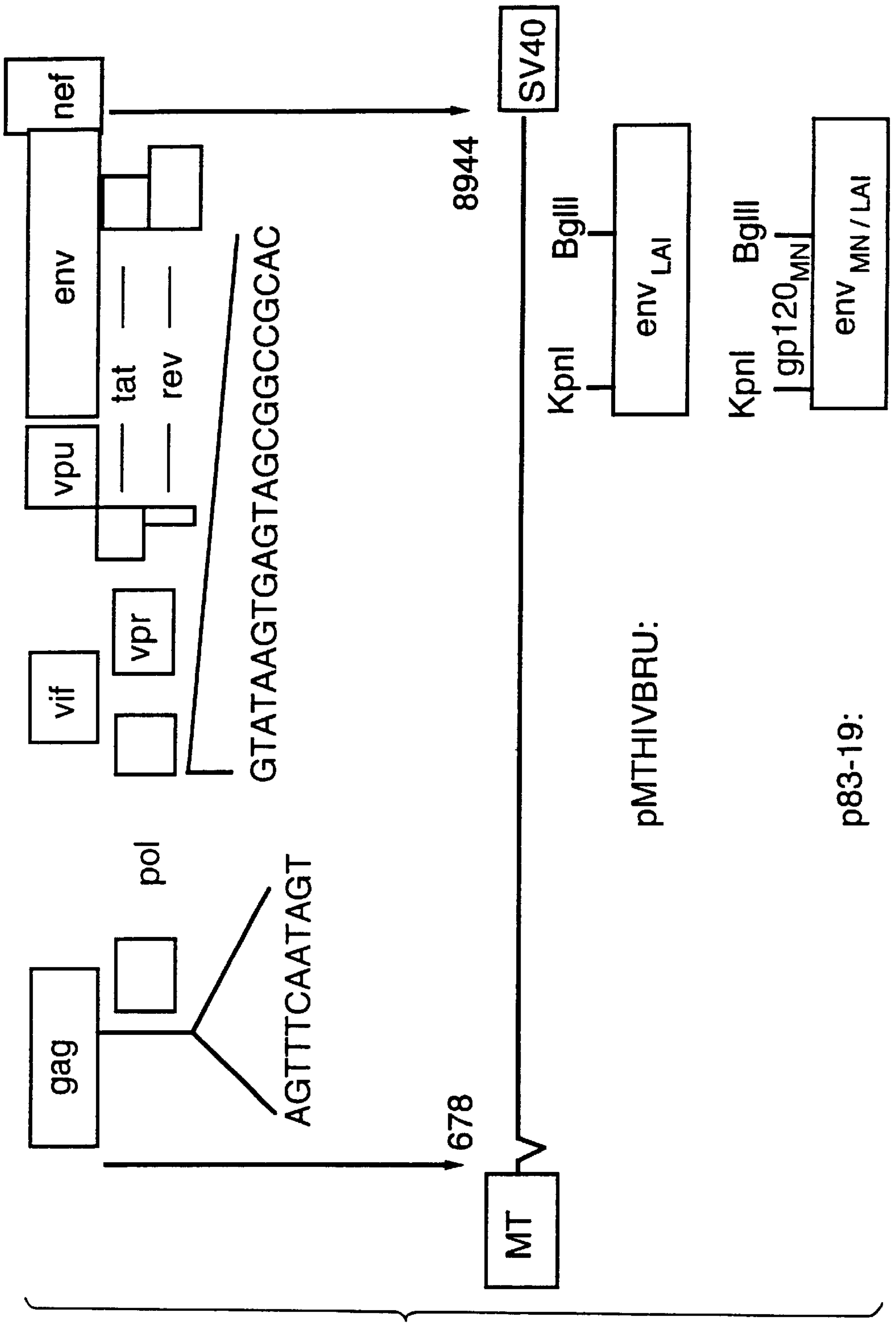
FIG. 3 shows a construction scheme of a plasmid (p83-19) encoding a retrovirus-like particle having a modification in the env gene product in accordance with a further embodiment of the invention.

Plasmid pMTHIVBRU encodes an HIV-like particle with an envelope protein corresponding to that of the HIV-$1_{LAI}$ isolate. Referring to FIG. 3, there is shown a plasmid p83-19 in which the LAI envelope of pMTHIVBRU has been substantially replaced by the MN envelope sequence. Thus, plasmid p83-19 encodes an HIV-like particle deficient in a plurality of elements required for infectivity and/or replication of HIV but dispensible for virus-like particle production, and contains as the env gene product substantially the envelope of HIV-1 isolate MN.

Figure 4:
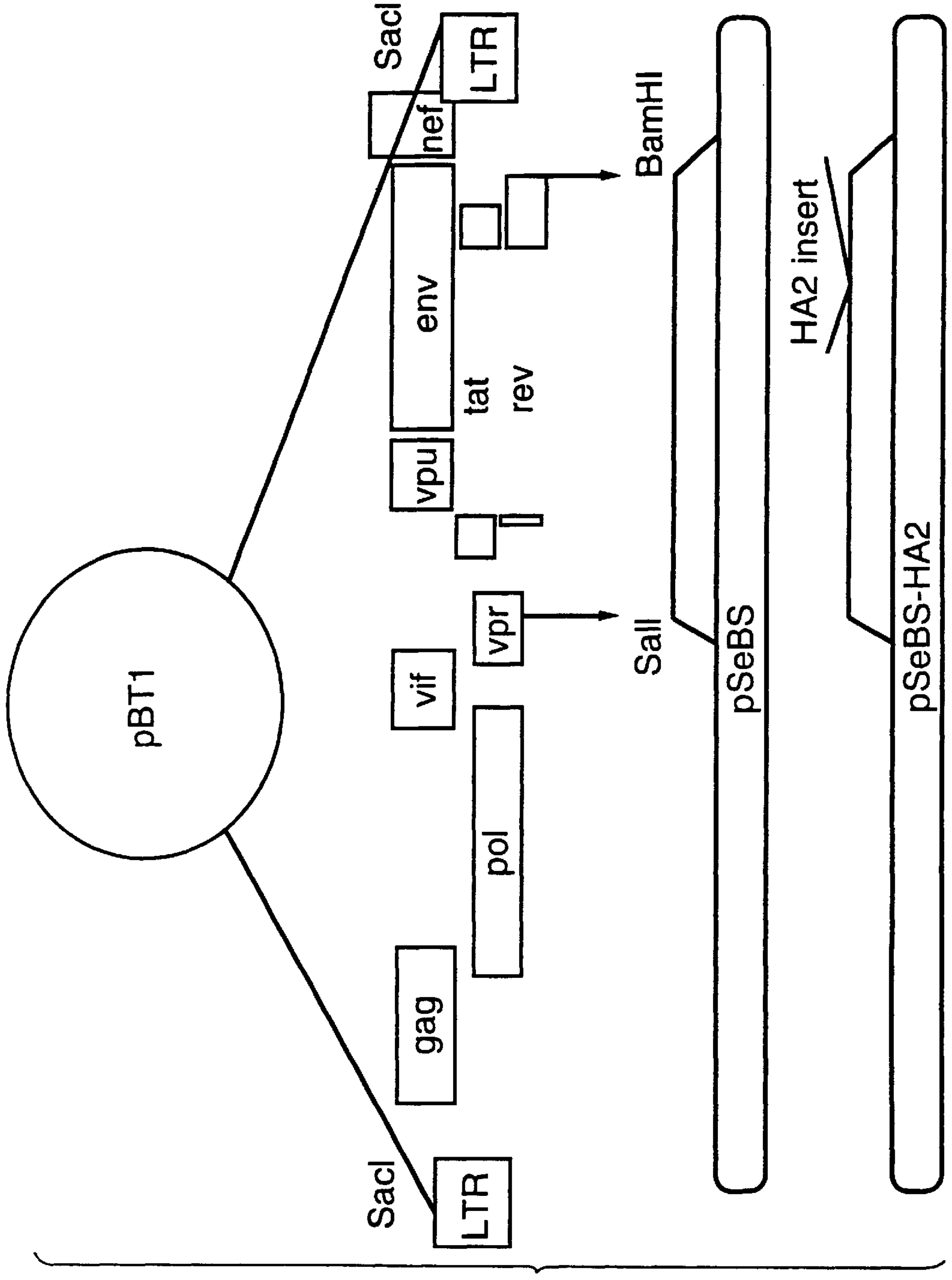
FIG. 4 shows a construction scheme of plasmid pSeBS-HA2 containing a heterologous anchor sequence in the env gene.
Figure 5:
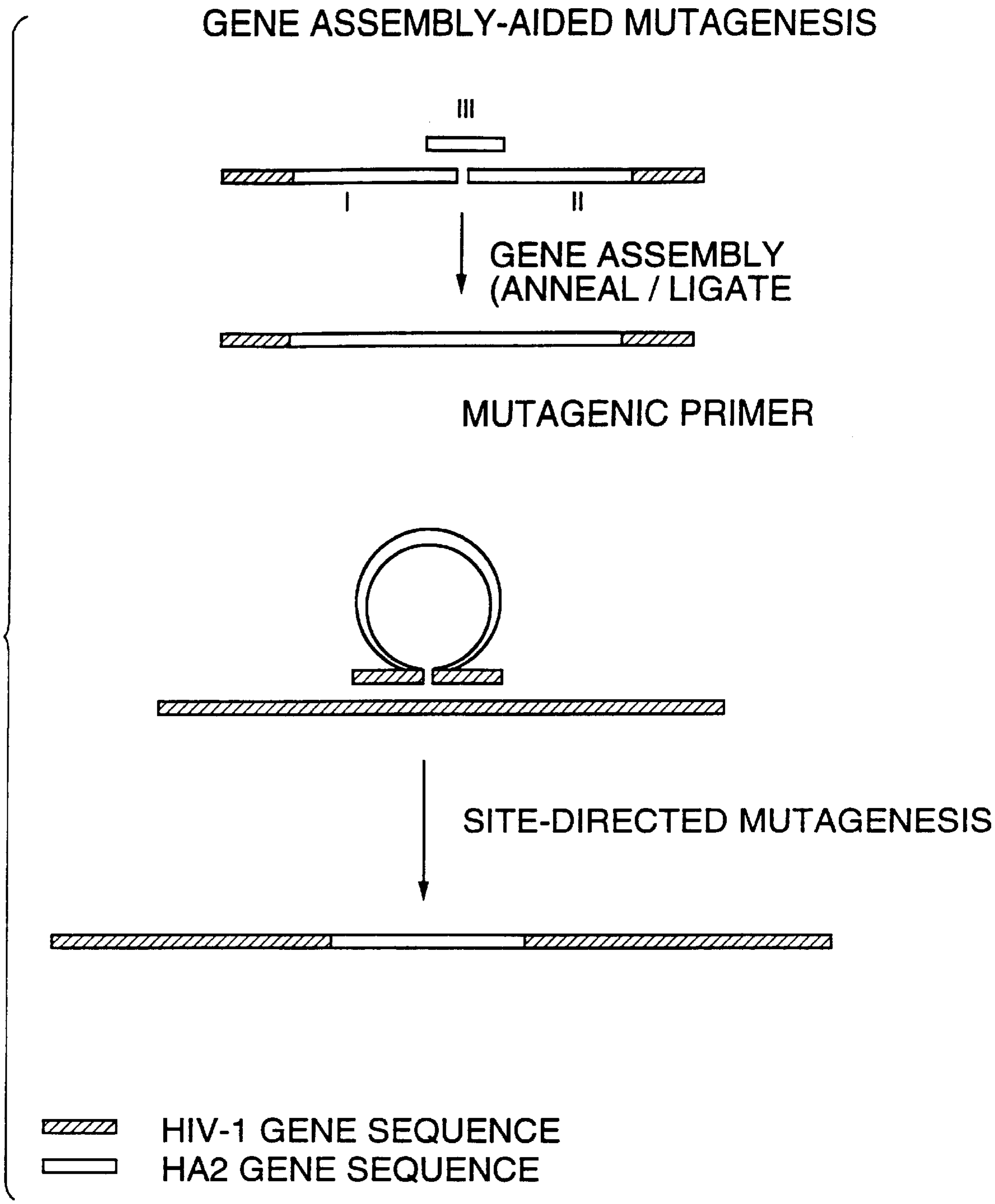
FIG. 5 shows a flow diagram for gene assembly-aided mutagenesis.
Figure 6:
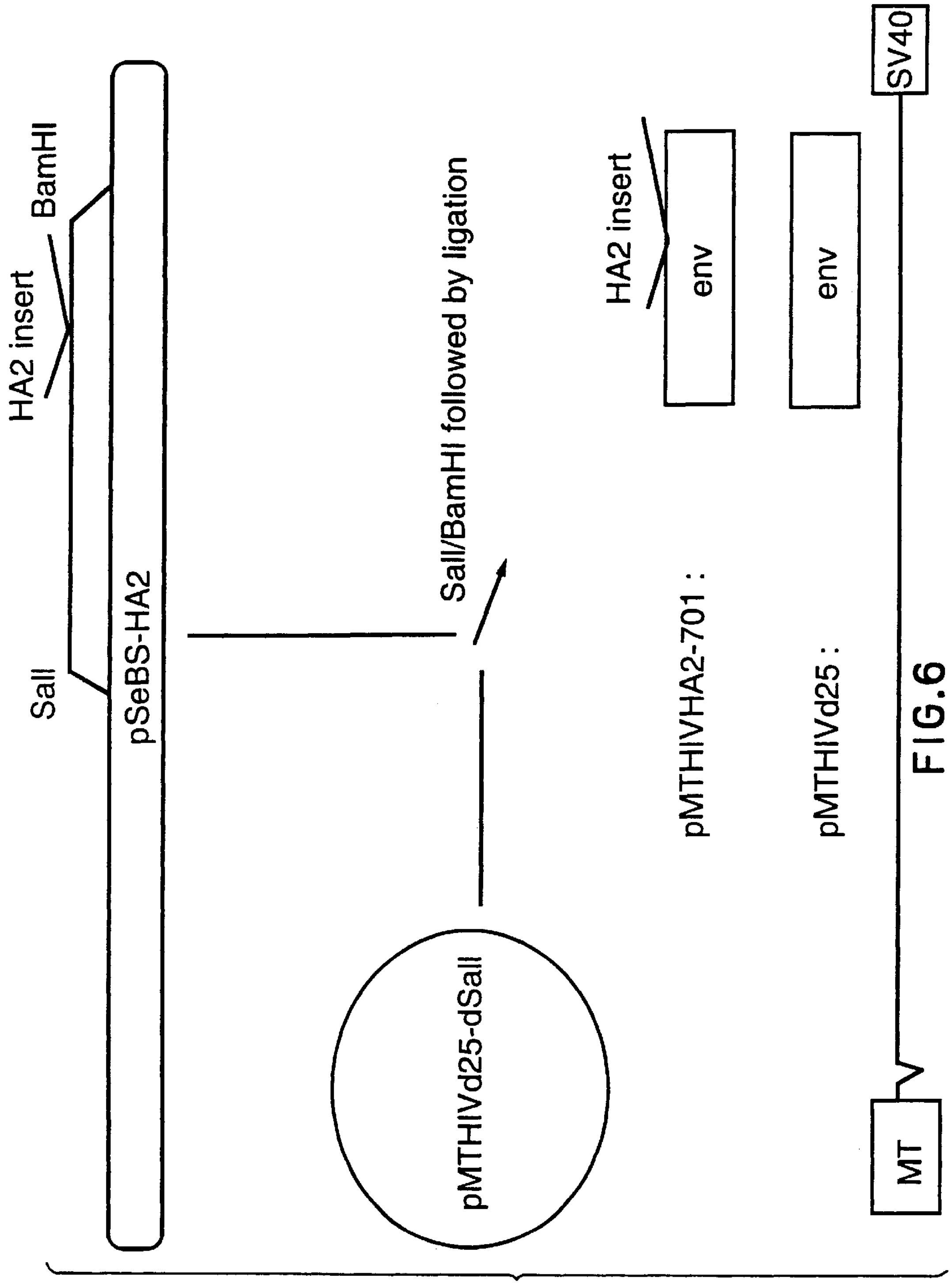
FIG. 6 shows a construction scheme of a plasmid (pMTHIVHA2-701) encoding a retrovirus-like particle containing an antigenic marker. comprising a portion of the transmembrane component of human influenza hemagglutinin glycoprotein.

Referring to FIGS. 4 to 6, there is illustrated the construction of a vector pMTHIVHA2-701 containing a modified HIV genome deficient in long terminal repeats, primer binding site and an RNA packaging sequence, and containing gag, pol and env genes in their natural genomic arrangement. The env gene in pMTHIVHA2-701 has been modified to provide therein a gene encoding a different anchor sequence to anchor the env gene product to the retrovirus-like product, whereby the modified env gene encodes a modified env gene product in which endogenous anchoring function of env has been replaced by the different anchor sequence. In retrovirus-like particles encoded by pMTHIVHA2-701 an immunodominant epitope of gp41 (which provides endogenous anchoring function) is no longer expressed. Thus, such retrovirus-like particles are antigenically marked in a negative manner by the absence of an amino acid sequence corresponding to an epitope of a retroviral protein. The different anchor sequence may itself be antigenic to further provide a positive non-retroviral or non-HIV retroviral antigenic marker for the retrovirus-like particles.

In this particular illustrated embodiment of the invention, a 135-bp sequence comprising a coding DNA fragment and a stop codon from the human influenza virus HA2 gene was inserted between nucleotides 7777 (G) and 7778 (A) of the HIV-$1_{LAI}$ envelope gene to prevent synthesis of the HIV-$1_{LAI}$ gp41 transmembrane glycoprotein. Plasmid pMTHIVHA2-701 thus encodes an HIV-like particle wherein the gp41 transmembrane glycoprotein anchoring function has been replaced by an anchor sequence from the human influenza virus HA2 protein and the HA2 protein further provides an antigenic marker.

Figure 7:
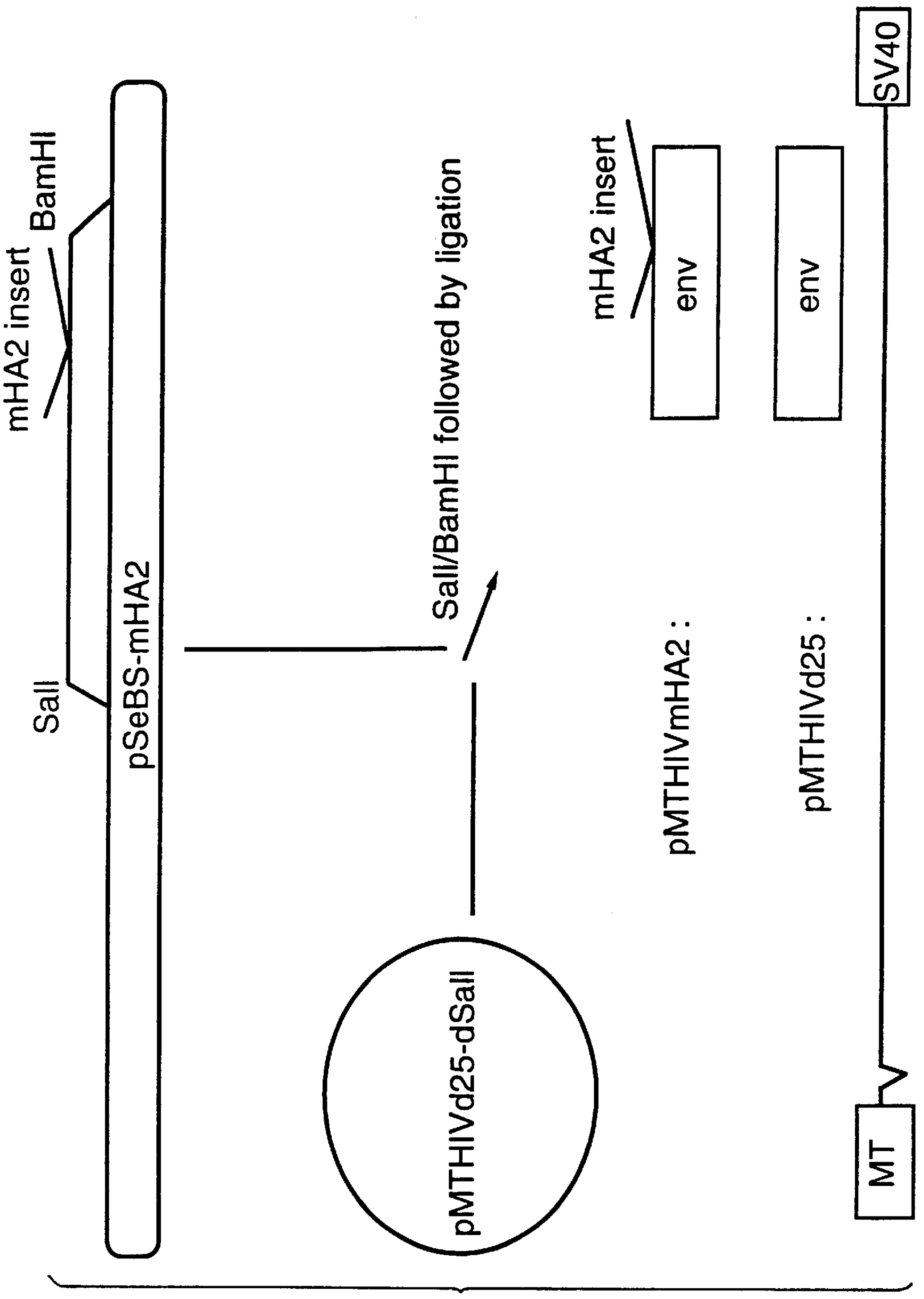
FIG. 7 shows a construction scheme of a plasmid (pMTHIVmHA2) encoding a retrovirus-like particle containing a non-naturally occurring marker.

Referring to FIG. 7, there is illustrated plasmid pMTHIVmHA2 which is similar to pMTHIVHA2-701 but contains as the antigenic marker sequence replacing the endogenous anchoring function of env, an amino acid sequence with no homology to known naturally occurring proteins.

Figure 8:
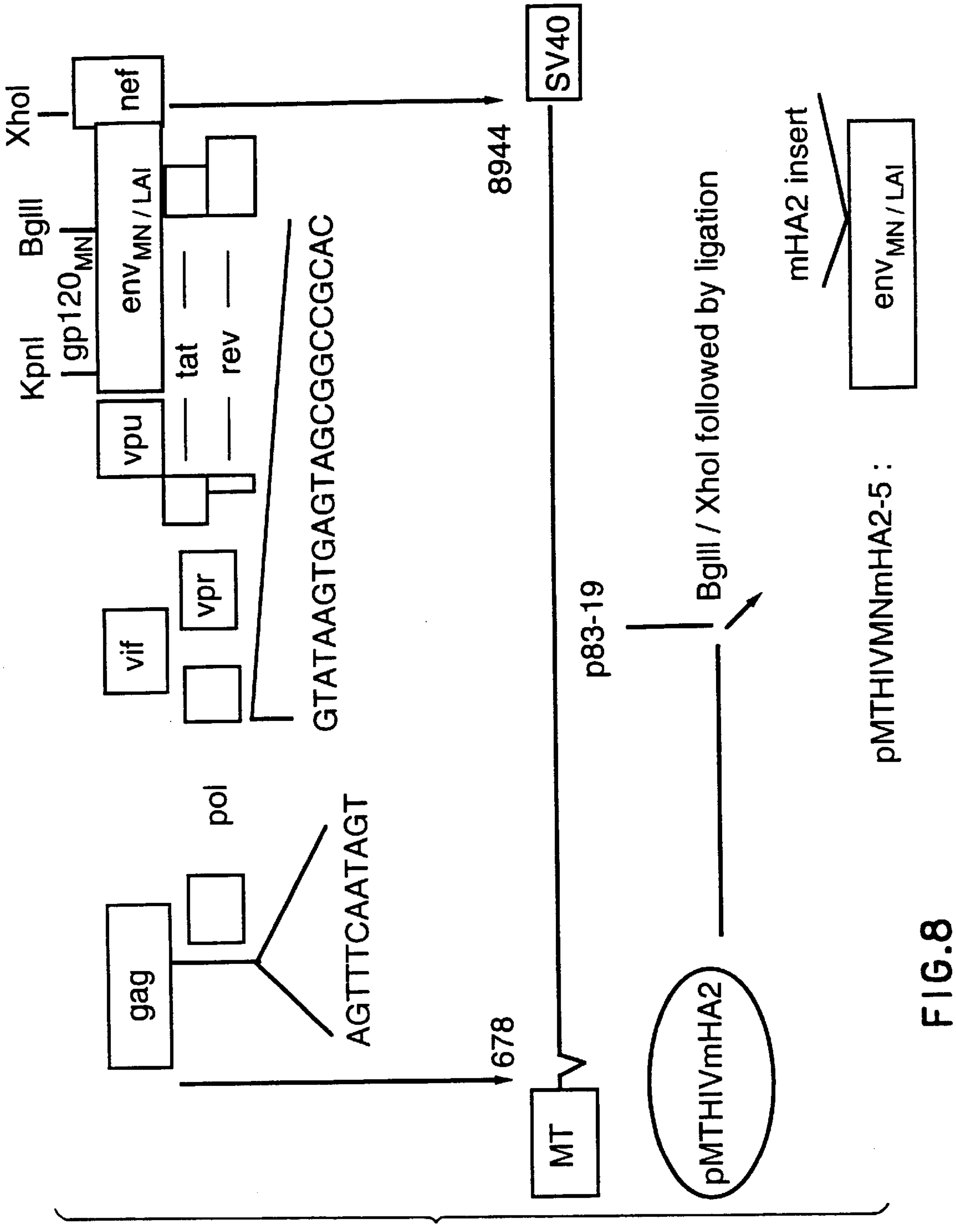
FIG. 8 shows a construction scheme for a plasmid (pMTHIVMNmHA2-5) encoding a retrovirus-like particle containing a non-naturally occurring marker.

Referring to FIG. 8, there is illustrated a vector pMTHIVMNmHA2-5 (ATCC designation 75853) containing a modified HIV genome deficient in long terminal repeats, primer binding site and an RNA packaging sequence and containing gag, pol and env genes in their natural genomic arrangement. The pol gene of pMTHIVMNmHA2-5 has been modified by deletion of a portion thereof to substantially remove the reverse transcriptase and integrase activities thereof. Furthermore, an oligonucleotide was inserted within the deleted pol gene to introduce three stop codons in three different reading frames to prevent remaining sequences of integrase from being translated. The gag gene of pMTHIVMNmHA2-5 has also been modified to replace the two cysteine residues in the first Cys-His box of gag by serines. In pMTHIVMNmHA2-5, the endogenous anchoring function of env has been replaced by an amino acid sequence with no known homology to naturally occurring proteins. HIV-like particles produced from Vero cells (and other vaccine-quality cell lives, including MCR5 cells, primary monkey kidney (African Green) cells, WI38 cells and baby hamster kidney cells) transfected with plasmid pMTHIVMNmHA2-5 were purified and used to immunize guinea pigs. Antisera were collected and assayed by ELISA for anti-V3 (i.e. anti-envelope) antibodies and anti-mHA2 (i.e. anti-antigenic marker) antibodies as shown in Table 1. These results indicate that the env gene product is present in substantially its native conformation and that the antigenic marker is immunogenic.

Although particular retrovirus-like particles have been described in which endogenous anchoring function of env has been replaced by the antigenic anchor sequence of particular natural and unnatural proteins, it is appreciated that many variations, adaptations and modifications can be made to the particular means by which the endogenous anchoring function can be replaced without departing from the essence of the invention.

Figure 9:
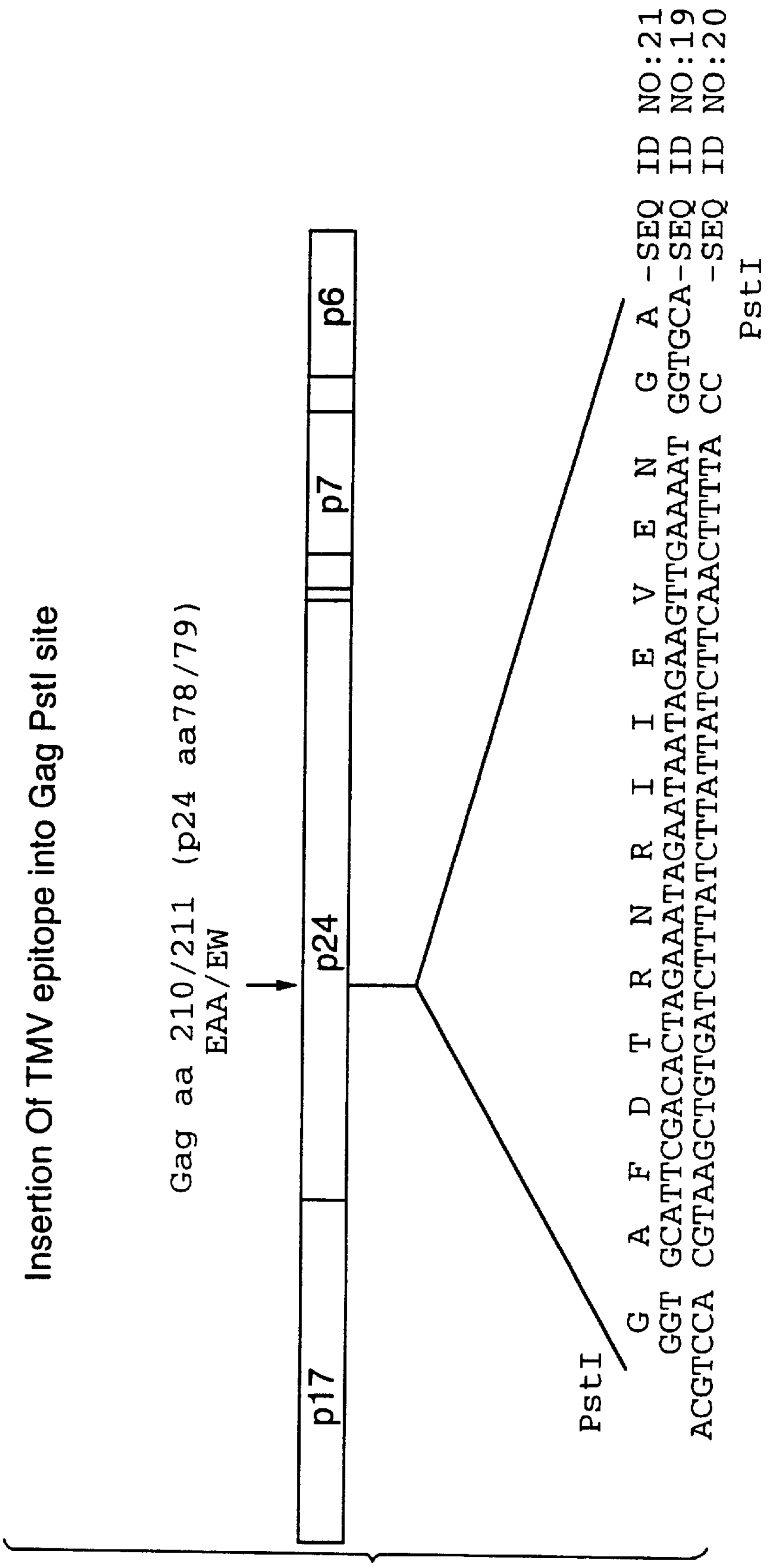
FIG. 9 shows details of an oligonucleotide encoding an antigenic epitope from tobacco mosaic virus inserted into the gag gene product of a non-infectious non-replicating retrovirus-like particle.
Figure 10:
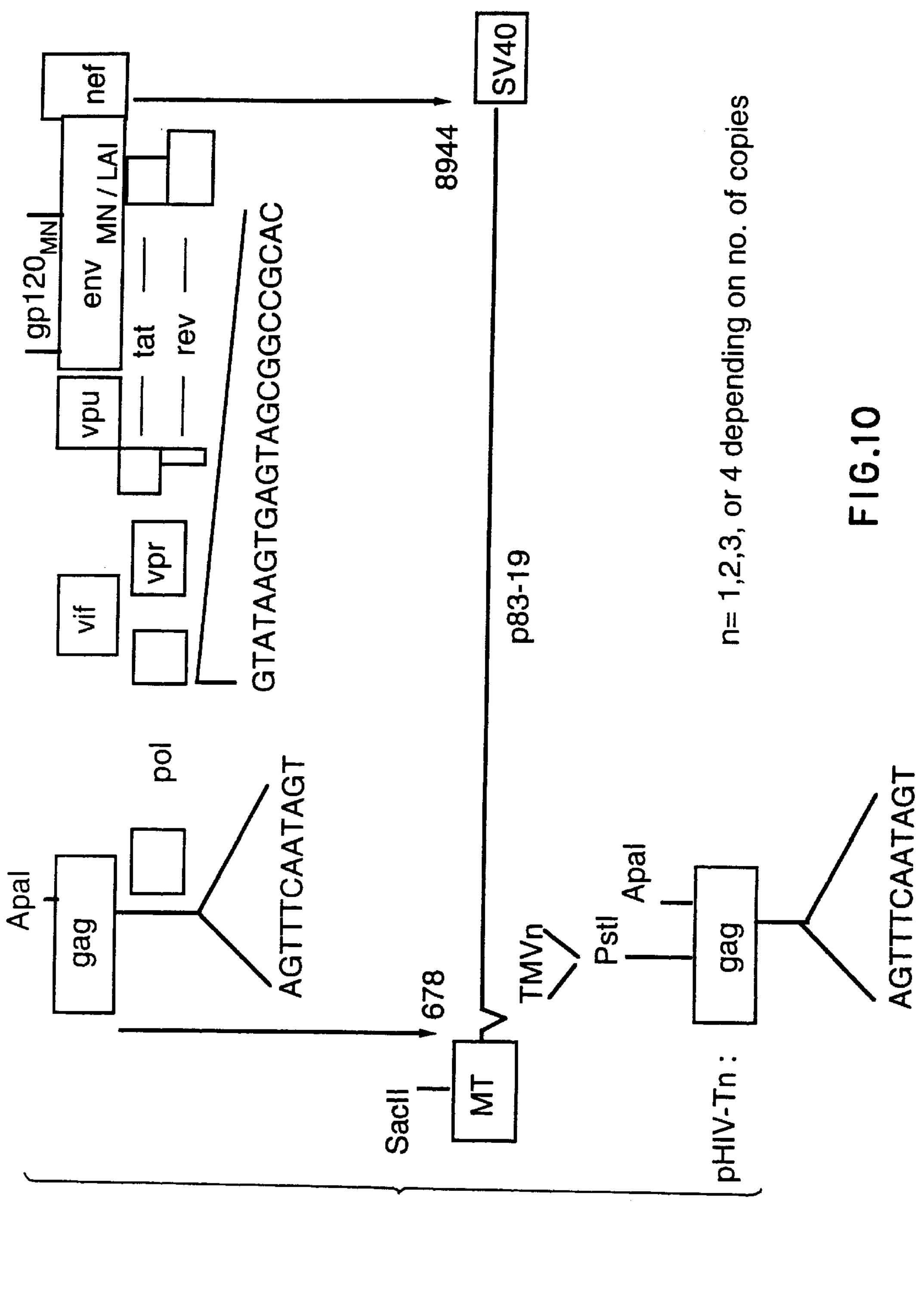
FIG. 10 shows a construction scheme of plasmids encoding retrovirus-like particles having antigenic epitopes from tobacco mosaic virus.
Figure 12:
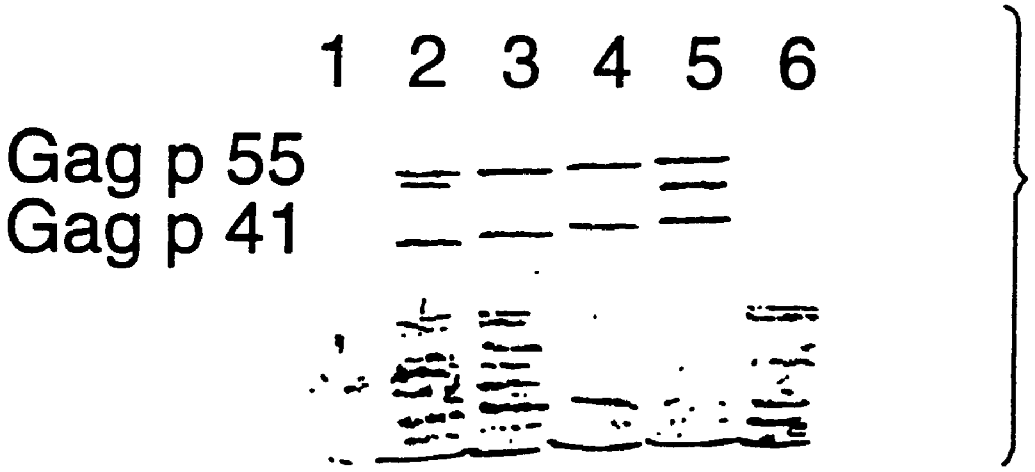
FIG. 12 shows an immunoblot analysis of antigenically marked. retrovirus-like particles to demonstrate inclusion of the antigenic marker in the gag gene product.

Referring to FIGS. 9 and 10, there is illustrated plasmids (pHIV-T1; pHIV-T2; pHIV-T3 and pHIV-T4) containing between one and four copies of a DNA sequence encoding an antigenic epitope from TMV. In the particular embodiments shown, the TMV epitope is inserted into the gag gene of HIV to produce a hybrid gag gene product, and the plasmids are deficient in the plurality of elements required for infectivity and/or replication of HIV but dispensible for virus-like particle production as described above. Stable cell lines were produced using plasmids pHIV-T1, pHIV-T2 (ATCC designation 75852), pHIV-T3 and pHIV-T4 (containing 1, 2, 3 and 4 copies of the antigen epitope, respectively) that produced HIV-like particles containing the antigenic marker inserted into the gag protein. These HIV-like particles were purified and their reactivity with anti-HIV monoclonal antibodies (FIG. 11) and anti-TMV marker antiserum (FIG. 12) determined. The results are shown in FIGS. 11 and 12 and indicate that the HIV-like particles contain gp120, gp41 and p24 in substantially their natural conformations and that the TMV marker is able to be recognized by anti-marker antibodies.

While specific embodiments of the marker sequences, which may also be an anchor sequence, are described herein, it is apparent that any other convenient amino acid sequence providing marker and/or anchoring function may be employed herein, including the absence of an amino acid sequence that corresponds to an epitope of a retroviral pollen. The amino acid sequence providing marker function may comprise a non-naturally occurring antigenic sequence which has no homology to known protein. An example of such sequence is the mutant HA2 sequence described above. Other examples may include antigenic regions of non-human or non-mammalian protein, such as non-human or non-mammalia pathogenic or comensual organisms. An example of such sequence is the TMV described above.

It is clearly apparent to one skilled in the art, that the various embodiments of the present invention have many applications in the fields of vaccination, diagnosis, treatment of HIV infections, and the generation of immunological reagents. A further non-limiting discussion of such uses is further presented below.

Vaccine Preparation and Use

It has been shown that an immunogenic preparation in accordance with the invention can elicit an immune response. One possible use of the present invention is, therefore, as the basis of a potential vaccine against retroviral diseases including AIDS and AIDS-related conditions. In a further aspect, the invention thus provides a vaccine against AIDS and AIDS-related conditions, comprising an immunogenic composition in accordance with the invention.

Immunogenic compositions, suitable to be used as vaccines, may be prepared from non-infectious retrovirus-like particles as disclosed herein. The immunogenic composition elicits an immune response which produces antibodies that are antiviral. Should the vaccinated subject be challenged by a retrovirus, such as HIV, the antibodies bind to the virus and thereby inactivate it.

Vaccines may be prepared as injectables, as liquid solutions or emulsions. The non-infectious retrovirus-like particles may be mixed with pharmaceutically-acceptable excipients which are compatible with the retrovirus-like particles. Excipients may include water, saline, dextrose, glycerol, ethanol, and combinations thereof. The vaccine may further contain auxiliary substances, such as wetting or emulsifying agents, pH buffering agents, or adjuvants to enhance the effectiveness of the vaccines. Methods of achieving an adjuvant effect for the vaccine include the use of agents, such as aluminum hydroxide or phosphate (alum), commonly used as 0.05 to 0.1 percent solution in phosphate buffered saline and other adjuvants, including QS21 and incomplete Freunds adjuvant. Vaccines may be administered parenterally, by injection subcutaneously or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkalene glycols or triglycerides. Oral formulations may include normally employed incipients, such as pharmaceutical grades of saccharine, cellulose and magnesium carbonate. These compositions take the form of solutions, suspensions, tablets, pills, capsules, sustained-release formulations or powders and contain 10 to 95% of the retrovirus-like particles of the invention.

The vaccines are administered in a manner compatible with the dosage formulation, and in such amount as is therapeutically effective, protective and immunogenic. The quantity to be administered depends on the subject to be treated, including, for example, the capacity of the individual's immune system to synthesize antibodies, and to produce a cell-mediated immune response. Precise amounts of active ingredient required to be administered depend on the judgment of the practitioner. However, suitable dosage ranges are readily determinable by one skilled in the art and may be of the order of micrograms of the retrovirus-like particles. Suitable regimes for initial administration and booster doses are also variable, but may include an initial administration followed by subsequent administrations. One example of an immunization schedule is at least one pre-immunization with a retrovirus-like particle, according to the present invention followed by at least one secondary immunization with a synthetic peptide described in published European Patent Publication Number 0 570 980, assigned to the assignee hereof. The dosage of the vaccine may also depend on the route of administration and will also vary according to the size of the host.

Nucleic acid molecules encoding the retrovirus-like particles of the present invention may also be used directly for immunization by administration of the nucleic acid molecules directly, for example by injection to a host. Processes for the direct injection of DNA into test subjects for genetic immunization are described in, for example, Ulmer et al, 1993 (a list of references appears at the end of the disclosure and each of the listed references is incorporated by reference without further reference thereto).

Molecules in accordance with the invention may further find use in the treatment (prophylactic or curative) of AIDS and related conditions, by acting either to displace the binding of the HIV virus to human or animal cells or by disturbing the 3-dimensional organization of the virus.

A further aspect of the invention thus provides a method for the prophylaxis or treatment of AIDS or related conditions, comprising administering an effective amount of an immunogenic composition in accordance with the invention.

Immunoassays

The retrovirus-like particles of the present invention are useful as immunogens, as antigens in immunoassays including enzyme-linked immunosorbent assays (ELISA), RIAs and other non-enzyme linked antibody binding assays, or procedures known in the art for the detection of anti-retroviral (for example, HIV) HIV antibodies and retroviral antigen (for example, HIV). In ELISA assays, the retrovirus-like particles are immobilized onto a selected surface, for example a surface capable of binding proteins, such as the wells of a polystyrene microtitre plate. After washing to remove incompletely adsorbed retrovirus-like particles, a non-specific protein, such as a solution of bovine serum albumin (BSA) or casein, that is known to be antigenically neutral with regard to the test sample may be bound to the selected surface. This allows for blocking of non-specific adsorption sites on the immobilizing surface and thus decreases the background caused by non-specific bindings of antisera onto the surface.

The immobilizing surface is then contacted with a sample, such as clinical or biological materials to be tested, in a manner conducive to immune complex (antigen/antibody) formation. This may include diluting the sample with diluents, such as solutions of BSA, bovine gamma globulin (BGG) and/or phosphate buffered saline (PBS)/Tween. The sample is then allowed to incubate for from about 2 to 4 hours, at temperatures such as of the order of about 25° to 37° C. Following incubation, the sample-contacted surface is washed to remove non-immunocomplexed material. The washing procedure may include washing with a solution, such as PBS/Tween, or a borate buffer.

Following formation of specific immunocomplexes between the test sample and the bound retrovirus-like particles, and subsequent washing, the occurrence, and even amount, of immunocomplex formation may be determined by subjecting the immunocomplex to a second antibody having specificity for the first antibody. If the test sample is of human origin, the second antibody is an antibody having specificity for human immunoglobulins and in general IgG. To provide detecting means, the second antibody may have an associated activity, such as an enzymatic activity that will generate, for example, a colour development upon incubating with a[008e] appropriate chromogenic substrate. Quantification may then be achieved by measuring the degree of colour generation using, for example, a visible spectra spectrophotometer.

In one diagnostic embodiment where it is desirable to identify antibodies that recognize a plurality of HIV isolates, a plurality of immunologically distinct retrovirus-like particles of the present invention are immobilized onto the selected surface. Alternatively, when the anti-HIV antibodies recognize epitopes that are highly conserved among various HIV isolates (for example, a B-cell epitope from gag or gp41) a single or a limited number of retrovirus-like particles may be immobilized. In a further diagnostic embodiment where it is desirable to specifically identify antibodies that recognize a single HIV isolate (for example, LAI, MN, SF2 or HXB2) a single particular retrovirus-like particle of the present invention may be immobilized. This further diagnostic embodiment has particular utility in the fields of medicine, clinical trials, law and forensic science where it may be critical to determine the particular HIV isolate that was responsible for the generation of an immune response including an antibody response.

In a further diagnostic embodiment, it may be desirable to specifically identify immunologically distinct retroviruses, for example, HIV isolates that belong to different clades. Immunologically distinct HIV isolates may include for example, LAI, MN, SF2, HXB2 or a primary HIV-1 isolate. In this diagnostic embodiment, a particular retrovirus-like particle of the present invention is useful for generating antibodies including monoclonal antibodies that specifically recognize such an immunologically distinct HIV isolate.

It is understood that a mixture of immunologically distinct retrovirus-like particles may be used either as an immunogen in, for example, a vaccine or as a diagnostic agent. There may be circumstances where a mixture of retrovirus-like particles are used to provide cross-isolate protection and/or diagnosis. In this instance, the mixture of immunogens is commonly referred to as a "cocktail" preparation.

The present invention advantageously provides retrovirus-like particles comprising car, pol and env gene products substantially in their natural conformations. Such retrovirus particles will thus be recognized by conformational anti-HIV antibodies (such as anti-env antibodies) that may not recognize the HIV antigen in a denatured form or a synthetic peptide corresponding to such an HIV antigen. The retrovirus-like particles of the invention are therefore particularly useful as antigens and as immunogens in the generation of anti-retroviral antibodies (including monoclonal antibodies) in diagnostic embodiments.

In addition, the presence of the marker generates a specific immune response thereto the detection of which by the methods described above enables the ready distinction between immunization of a host with the immunogenic compositions provided herein compared to material infection by a virulent retrovirus. The ability to effect such diagnosis and differentiation has advantageous utility in the fields of epidemiology, clinical trials, forensic science and immunology.

Other Uses

Molecules which bind to the retrovirus-like particles on which the invention is based, particularly antibodies, antibody-related molecules and structural analogs thereof, are also of possible use as agents in the treatment and diagnosis of AIDS and related conditions.

Variants of antibodies (including variants of antigen binding site), such as chimeric antibodies, humanized antibodies, veneered antibodies, and engineered antibodies that are specific for the retrovirus-like particles of the invention are included within the scope of the invention.

Antibodies and other molecules which bind to the retrovirus-like particles of the present invention can be used for therapeutic (prophylactic and curative) and diagnostic purposes in a number of different ways, including the following:

For passive immunization by suitable administration of antibodies, possibly humanized antibodies, to HIV infected patients.

To activate, complement or mediate antibody dependent cellular cytotoxicity (ADCC) by use of antibodies of suitable subclass or isotype (possibly obtained by appropriate antibody engineering) to be capable of performing the desired function.

For targeted delivery of toxins or other agents, for example, by use of immunotoxins comprising conjugates of antibody and a cytotoxic moiety, for binding directly or indirectly to cell-surface exposed HIV proteins of HIV-infected cells (for example, gp120).

For targeted delivery of highly immunogenic materials to the surface of HIV-infected cells, leading to possible ablation of such cells by either the humoral or cellular immune system of the host.

For detection of HIV, using a variety of immunoassay techniques.

Thus, in yet a further diagnostic embodiment, the immunogenic compositions of the present invention (individually, or as mixtures including cocktail preparations) are useful for the generation of HIV antigen specific antibodies (including monoclonal antibodies) that can be used to detect HIV or antigens, or neutralize HIV in samples including biological samples.

In an alternative diagnostic embodiment, the retrovirus-like particles of the present invention can be used to specifically stimulate HIV specific T-cells in biological samples from, for example, HIV-infected individuals for diagnosis or therapy.

Biological Deposits

Certain plasmids that encode retrovirus-like particles according to aspects of the present invention that are described and referred to herein have been deposited with the American Type Culture Collection (ATCC) located at Rockville, Md. USA pursuant to the Budapest Treaty and prior to the filing of this application. Samples of the deposited plasmids will become available to the public upon grant of a patent based upon this United States patent application. The invention described and claimed herein is not to be limited in scope by plasmids deposited, since the deposited embodiment is intended only as an illustration of the invention. Any equivalent or similar plasmids that encode similar or equivalent retrovirus-like particles as described in this application are within the scope of the invention.

Deposit Summary

| Plasmid | ATCC Designation | Date Deposited |
|---|---|---|
| pMTHIVBRU | 75,852 | August 4, 1994 |
| pMTHIVMNmHA2-5 | 75,853 | August 4, 1994 |
| pHIV-T2 | 75,851 | August 4, 1994 |

The above disclosure generally describes the present invention. A more complete understanding can be obtained by reference to the following specific Examples. These Examples are described solely for purposes of illustration and are not intended to limit the scope of the invention. Although specific terms have been employed herein, such terms are intended in a descriptive sense and not for purposes of limitations. Immunological and recombinant DNA methods may not be explicitly described in this disclosure but are well within the scope of those skilled in the art.

EXAMPLES

Methods of molecular genetics, protein biochemistry, and immunology used but not explicitly described in this disclosure and these EXAMPLES are amply reported in the scientific literature and are well within the ability of those skilled in the art.

Example 1

This Example describes the construction of plasmid pMTHIVBRU.

Plasmid pMTHIVBRU was constructed as shown in FIGS. 1 and 2. This plasmid is a modification of the expression vector pMTHIVd25 described in Rovinski et al 1992 (the literature references are identified at the end of the specification) and which contains an RNA packaging deletion, and was engineered to contain a series of mutations/deletions. Thus, a Cys-His box mutation included replacements of two cysteine codons (in SEQ ID NO: 13) with two serine codons in the first Cys-His box (SEQ ID NO: 14) of the gag protein as shown in FIG. 1. This was accomplished by a PCR-based mutagenesis method. Two primers were synthesized: the upstream primer having the sequence 5'-GGACTAGTACCCTTCAGGAACAAATAGGATGG ATGACAAA TAATCCACCTATCCCAGTAGGAG-3' (SEQ ID NO: 15), comprising nucleotides 1,507 to 1,567 of HIV-$1_{LAI}$, (all nucleotide numbering is according to Wain- Hobson et al., 1985) with a SpeI site at the 5'-end; and the downstream primer having the sequence 5' CTCGGGCCCT-GCAATTTCTGGCTATGTGCCCTTC TTTGCCACTATTGAAACTCTTAACAATC-3' (SEQ ID NO: 16), being the reverse complement of nucleotides 2,011 to 1,953 with an ApaI site at the 5'-end. In the downstream primer, two adenosine residues representing the reverse complement of nucleotides 1,963 and 1,972 (Wain Hobson et al, 1985; Myers etal, 1990) were changed to thymidine, resulting in the replacement of the two cysteines at amino acid positions 392 and 395 of the gag gene product with two serines (FIG. 1). These two primers were used to amplify the SpeI-ApaI DNA fragment (nucleotides 1507 to 2006) of pMTHIV (Rovinski et al, 1992) which was used as a template. The PCR-amplified SpeI-ApaI fragment was purified by agarose gel electrophoresis and digested with restriction enzymes SpeI and ApaI. This fragment was used to replace the corresponding fragment in pMTHIVd25 (Rovinski et al, 1992). The resulting plasmid was named pMTHIV-A, which contains both the RNA packaging sequence deletion and the Cys-His box mutation.

In order to delete the reverse transcriptase and integrase, two BalI recognition sites at nucleotides 2,655 and 4,587 of HIV-$1_{LAI}$, were used (FIG. 2). The 1.9-kbp fragment between the two BalI sites contains DNA sequences encoding more than 95% of the reverse transcriptase and the first 108 amino acids of the integrase. The plasmid pMTHIV-A was digested with BalI. After removing the 1.9-kbp BalI fragment by gel electrophoresis, the remaining portion of the plasmid was ligated with a double-stranded oligonucleotide: 5'-GTATAAGTGAGTAGCGGCCGCAC-3' (only one strand is shown—SEQ ID NO: 17) which contains three stop codons in three different reading frames to prevent the remaining sequences of integrase from being translated. The resulting plasmid was termed pMTHIVBRU.

Example 2

This Example describes the construction of plasmids encoding HIV-like particles containing antigenically marked envelope anchors.

Plasmid p83-19 was constructed from expression vector pMTHIVBRU, as shown in FIG. 3. This plasmid contains a hybrid envelope gene which was engineered by replacing DNA encoding most of $gp120_{LAI}$, with the cognate DNA encoding $gp120_{MN}$. This was accomplished by replacing a KpnI/BglII DNA fragment (nucleotides 6379 to 7668) from HIV-$1_{LAI}$, with a KpnI/BglII DNA fragment (nucleotides 6358 to 7641) from HIV-$1_{MN}$.

Plasmid pMTHIVHA2-701 was constructed from expression vectors pBT1 (Alizon et al, 1984) and pMTHIVd25 (Rovinski et al, 1992), as shown in FIGS. 4 to 6. The pMTHIVHA2-701 vector contains a 135-bp sequence comprising a coding DNA fragment and a stop codon from the human influenza virus HA2 gene (Min Jou et al, 1980), inserted between nucleotides 7777(G) and 7778(A) of the HIV-$1_{LAI}$ envelope gene (Wain-Hobson et al, 1985; Myers et al, 1990). The stop codon was inserted to prevent synthesis of the HIV-$1_{LAI}$ gp41 transmembrane glycoprotein. A SalI (nucleotide 5821)/BamHI (nucleotide 8522) DNA fragment from pBT1 was subcloned into pSelect (Promega) to produce pSeRS (FIG. 4). The latter plasmid was used for insertion of the 135-bp by a procedure termed herein as 'gene assembly-aided mutagenesis (GAAM)'. A mutagenic primer, which was designed to contain the 135-bp sequence comprising a coding DNA fragment from the human influenza virus HA2 gene (Min Jou et al, 1980), was assembled as shown in FIG. 5. Oligonucleotide I is a 99 mer containing (from 3' to 5') 30 bases complementary to nucleotides 7748 to 7777 of HIV-$1_{LAI}$ (Wain-Hobson et al, 1985; Myers et al, 1990) and 69 bases which are complementary to HA2 gene sequences (Min Jou et al, 1980) encoding amino acids 180 to 202 of the HA2 protein. Oligonucleotide II is a 96 mer comprising (from 3' to 5') i) 60 bases complementary to HA2 gene sequences which encode amino acids 203 to 221 of the HA2 protein and contain the HA2 stop codon (Min Jou et al, 1980), ii) 6 bases (ATCATT—SEQ ID NO: 18) defining two more stop codons, and iii) 30 bases complementary to nucleotides 7778 to 7807 of HIV-$1_{LAI}$, (Wain-Hobson et al, 1985; Myers et al, 1990). Oligonucleotide III is a bridging 30 mer having 15 nucleotides complementary to the 5'-end of oligonucleotide I and 15 nucleotides complementary to the 3'-end of oligonucleotide II. Ten picomoles of oligonucleotides I and II were mixed with 20 picomoles of oligonucleotide III and phosphorylated at 37° C. for 1.5 h in 20 $\mu$l kinase buffer (50 mM Tris-HCl, pH 7.5, 10 MM $MgCl_2$, 10 mm KCl, 5 MM DTT, and 0.5 MM ATP) containing 2 units of T4 polynucleotide kinase. The oligonucleotides were annealed by heating the mixture to 95° C. for 5 min and subsequently cooling it slowly to room temperature. To this mixture was added 3 $\mu$l of 10×ligase buffer (0.5 M Tris-HCl, pH 7.4, 0–1 M $MgCl_2$, 0.1 M DTT, 10 mM Spermidine, and 1 mg/ml BSA), 3 $\mu$l of 10 mM ATP, and 5 units of T4 DNA ligase, and the ligation mixture was incubated overnight at 16° C. to complete the assembly of the mutagenic primer (FIG. 5). This primer was used in the mutagenesis procedure without further purification.

Mutagenesis was performed using the Altered Sites in vitro Mutagenesis System from Promega (Madison, Wis.). The template for mutagenesis consisted of the pSeBS plasmid (FIG. 4) which contained the 2.7-kbp SalI/BamHI DNA fragment of the HIV-$1_{LAI}$ envelope gene (nucleotides 5821 to 8522) cloned into the pselect phagemid vector provided in the mutagenesis kit. Following the mutagenesis procedure, putative clones were identified by colony hybridization with a $^{32}$P-labelled oligonucleotide III probe. Positive clones were confirmed by DNA sequencing. One of these clones, designated pSeBS-HA2, was used for the construction of the final vector. To this end, the modified SalI/BamHI insertfrom pSeBS-HA2 was subcloned into pMTHIVd25-dSalI; the latter is a plasmid derived from pMTHIVd25 (Rovinski et al, 1992) by partial digestion with SalI followed by Klenow treatment to eliminate the SalI site within the plasmid backbone. The final expression construct was designated pMTHIVHA2-701.

An expression vector, pMTHIVmHA2 (shown in FIG. 7) containing a heterologous DNA sequence inserted between nucleotides 7777 (G) and 7778 (A) of the HIV-$1_{LAI}$ envelope gene (Rovinski et al, 1992; Wain-Hobson et al, 1985) was engineered as described above. In this case, a 134-bp sequence, comprising a coding DNA fragment from the human influenza virus HA2 gene (Min Jou et al, 1990) and 68 nucleotides that, when fused to the HA2 sequences, encodes an amino acid sequence with no homology to known naturally occurring proteins, was inserted downstream of nucleotide 7777 of HIV-$1_{LAI}$ (FIG. 7). The insertion resulted in a frameshift in the translation of HIV-$1_{LAI}$ coding sequences, and the creation of a stop codon (TAG) to prevent synthesis of the gp41 transmembrane glycoprotein of HIV-$1_{LAI}$. The final expression construct was designated pMTHIVmHA2 (FIG. 7).

Plasmid pMTHIVMNmHA2-5 was constructed from expression vectors p83-19 and pMTHIVmHA2 as shown in FIG. 8. This plasmid was designed to have all of the mutations of elements required for infectivity and/or replication of p83-19 and to contain the 134-bp insert sequence of pMTHIVmHA2 (FIG. 7). To this end, p83-19 was digested with BglII (nucleotide 7,641) and XhoI (nucleotide 8,944) to remove a 1276-bp DNA fragment which was replaced by the cognate BglII/XhoI fragment of pMTHIVmHA2.

Example 3

This Example describes the construction of plasmids encoding HIV-like particles containing antigenic epitopes from TMV.

Plasmids pHIV-T1, pHIV-T2, pHIV-T3, and pHIV-T4 represent modified versions of the p83-19 construct in that they contain, respectively, either one, two, three, or four copies of a double-stranded oligonucleotide (FIGS. 9, 10 and 11) comprising at least one antigenic epitope (Westhof et al, 1984; Trifilleff et al, 1991) from TMV coat protein. The construction of these four vectors is illustrated in FIGS. 9 and 10. To engineer all constructs, plasmid pMTHIV-A (FIG. 1) was first digested with SacII and ApaI to isolate a 1,328-bp DNA fragment which was then subcloned into pBluescript (Stratagene). The recombinant plasmid was then digested with PstI which cleaves HIV-$1_{LAI}$ DNA at nucleotide 1,415 within the gag gene. Subsequently, either one, two, three, or four copies of the double-stranded oligonucleotide shown in FIG. 9 (coding strand: SEQ ID NO: 19, complementary strand: SEQ ID NO: 20, encoded amino acids: SEQ ID NO: 21) were inserted into this restriction site. Finally, the resulting recombinant plasmids were digested with SacII and ApaI to release the modified insert which was then cloned into the cognate region of plasmid p83-19 (FIG. 10).

The expression of retrovirus-like particles containing either the mHA2 epitope or various copies of the TMV epitope is depicted in FIG. 11. Vero cells were grown to 80% confluency and transfected with 20 $\mu$g of plasmid DNA by the transfinity (BRL) calcium phosphate procedure. Culture supernatants were analyzed for protein expression at 48 h post-transfection. Culture media (10 ml) from cells transfected with individual expression constructs were collected and clarified by centrifugation at 2,000×g (sorvall RT 6000B; Dupont Company, Wilmington, Del.) for 15 min at 4° C. Retrovirus-like particles were isolated by ultracentrifugation. Pelleted particles were suspended to 40 $\mu$l of TNE, mixed with 10 $\mu$l of 5×Laemmli sample buffer and boiled for 3 min. Viral proteins were then separated by SDS PAGE and transferred to Immobilon membranes (Millipore, Bedford, Mass.). Membranes were blocked with BLOTTO buffer (PBS containing 5% Carnation instant nonfat dry milk, 0.0001% wt/vol thimerosal, and 0.01% vol/vol antifoam A emulsion) for 2 h at 25° C. and then incubated with appropriate dilutions of antibodies overnight at 4° C. Filters were then incubated with a goat anti-mouse immunoglobulin G antibody conjugated to alkaline phosphatase (Promega, Madison, Wis.) and reacted with the alkaline phosphatase chromogenic substrates nitroblue tetrazolium chloride and 5-bromo-4-chloro-3-indolyphosphate ρ-toluidine salt (BRL). A cocktail of anti-gp120, anti-gp41, and anti-p24 antibodies was used in Panel A. A mixture of anti-gp120 and anti-p24 antibodies was used in Panel B.

The results shown in FIG. 11 demonstrate that the antigenically marked HIV-like particles produce gp120, gp41 and p24 substantially in their natural conformations.

Example 4

This Example describes the immunogenicity and immunoreactivity of antigenically marked HIV-like particles.

One of plasmids pHIV-T1, pHIV-T2, pHIV-T3, or pHIV-T4 (FIG. 10) was co-transfected with plasmid pSV2neo into Vero cells, and stable cell lines were established that produce HIV-like particles. HIV-like particles were purified, and their reactivity to immune sera from guinea pigs immunized with a peptide corresponding to the TMV marker inserted into the gag gene product was determined by immuno blot analysis. To obtain the immune sera, guinea pigs were immunized with 100 $\mu$g of a peptide consisting of the TMV marker conjugated to KLH and adjuvanted in Freund's complete adjuvant. All animals were boosted three times at 3-week intervals with the same peptide adjuvanted in Freund's incomplete adjuvant. Immune sera were collected two weeks after the last booster shots. The results, presented in FIG. 12, illustrate the reactivity of the immune sera to various forms of the gag gene product present in the various HIV-like particles and demonstrate the antigenicity of the TMV marker in the context of a modified HIV-1-like particle.

Plasmid pMTHIVMNmHA2-5 was co-transfected with plasmid pSV2neo into Vero cells, and a stable cell line was established that produces HIV-like particles. HIV-like particles were then purified, and guinea pigs immunized with 10 $\mu$g of gag p24-equivalent amounts of HIV-like particles adjuvanted in Freund's complete adjuvant. All animals were boosted three times at 3-week intervals with HIV-like particles adjuvanted in Freund's incomplete adjuvant. Two weeks after the last booster shots, immune sera were collected and assayed by ELISA for anti-V3 and anti-mHA2 marker reactivities. The results, presented in Table 1 below, indicate that guinea pigs immunized with HIV-like particles containing the mHA2 marker produced antibodies capable of recognizing peptides representing the mHA2 marker (MHA-1) and V3 loop neutralization domains (CLTB56, CLTB71, and CLTB73) These data, therefore, demonstrate that the mHA2 marker is immunogenic when presented in the context of an HIV-like particle and that antibodies are also produced against the major neutralizing determinants of the V3 loops from different HIV isolates.

SUMMARY OF DISCLOSURE

In summary of this disclosure, the present invention provides certain non-infectious, non-replicating, retrovirus-like particles and nucleic acid molecules encoding them as, for example, immunogenic preparations useful for vaccination, the generation of retroviral-specific antisera and as antigens in diagnostic methods and kits. The retrovirus-like particles may have been rendered non-infectious by modifications to the pol and/or gag gene products. Particular retrovirus-like particles contain non-retroviral antigenic markers. Modifications are possible within the scope of this invention.

TABLE 1

The ability of retrovirus-like particles containing an antigenic marker to generate retroviral-specific immune response and a marker-specific immune response.

| PEPTIDE | SEQUENCE | SPECIFICITY | SEQ ID NO. | ELISA IgG TITRES[1] GP542 | GP543 | GP544 |
|---|---|---|---|---|---|---|
| MRA-1 | GPAKKATLGATFAFDSKEEWCREKKEQWE | mHA2 marker | 22 | 500 | 5,000 | 2,500 |
| CLTB56 | NKRKRIHIGPGRAFYTTKN | V3(MN) | 23 | 500 | 500 | 2,500 |
| CLTB71 | NTRKSIYIGPGRAFHTTGR | V3(SF2) | 24 | 500 | 2,500 | 2,500 |
| CLTB73 | NTRKRIRIQRGPGRAFVTIGK | V3(HXB2) | 25 | 500 | 1,000 | 2,500 |
| Irrelevant | MKKTRFVLNSIALGLSVLSTSFVAQATLPSFVSEQNS | Non-HIV | 26 | 100 | 100 | 100 |

[1]Each guinea pig (GP542, GP543 and GP544) was immunized as described in Example 4.

REFERENCES

1. Rovinski, B., Haynes, J. R., Cao, S. X., James, O., Sia, C., Zolla-Pazner, S., Matthews, T. J. and Klein, M. (1992) J. Virol., 66, 4003–4012.
2. Wain-Hobson, S., Sonigo, P., Danos, O., Col, S. and Alizon, M. (1985) Cell, 40, 9–17.
3. Myers, G., Berzofsky, J. A., Rabson, A. B., Smith, T. F. and Wong-Staal, F. (ed.) (1990) Human retroviruses and AIDS. Theoretical Biology and Biophysics, Group T-10. Los Alamos National Laboratory, Los Alamos, N.Mex.
4. Alizon, M., Sonigo, P., Barre-Sinoussi, F., Chermann, J. C., Tiollais, P., Montagnier, L. and Wain-Hobson, S. (1984) Nature, 312, 757–780.
5. Min Jou, W., Verhoeyen, M., Devos, R., Saman, E., Fang, R., Huylebroeck, D. and Fiers, W. (1980) Cell, 19, 683–696.
6. Westhof, E., Altschuh, D., Moras, D., Bloomer, A. C., Mondragon, A., Klug, A. and Van Regenmortel, M. H. (1984) Nature, 311, 123–126.
7. Trifilieff, E., Dubs, M. C. and Van Regenmortel, M. H. V. (1991) Mol. Immunol., 28, 889–896.
8. Kieny, M. P. (1990) J. Acquired Immune Deficiency Syndromes, 3, 395–402.
9. Ulmer, J. B., Donnelly, J. J. and Liu, M. A. (1993) Curr. Opin. Invest. Drugs 2(9), 983–989.

What we claim is:

1. A non-infectious immunogenic, non-replicating human immunodeficiency virus (HIV)-like particle containing a plurality of mutations in the viral genome resulting in a virus-like particle, comprising the following:

(1) a modified Gag protein, wherein said protein contains a modification, in the first Cys-His box only, wherein at least one amino acid residue has been replaced in said first Cys-His box, said replacement resulting in a reduction of gag-dependent genomic viral RNA packaging in the virus-like particle while retaining the immunogenicity of said virus-like particle;

(2) a deficient reverse transcriptase, wherein said deficiency results from a deletion of that portion of the pot gene responsible for reverse transcriptase activity, said deletion substantially eliminating reverse transcriptase activity in the virus-like particle;

(3) a deficient integrase, wherein said deficiency results from a deletion of that portion of the pol gene responsible for integrase activity, said deletion substantially eliminating integrase activity in the virus-like particle; and (4) a deficient RNase H, wherein the deficiency results from a deletion of that portion of the pot gene responsible for RNase H activity, said deletion substantially eliminating RNase H activity in the virus-like particle;

wherein said particle is encoded by a modified HIV genome devoid of long terminal repeats (LTRs) and containing the gag, pol and env genes in their natural genomic arrangement, and additionally comprising at least one non-retroviral, non-mammalian heterologous antigenic marker wherein said particle encoded by said modified HIV genome deficient in long terminal repeats is further modified by a heterologous nucleic acid insert encoding said at least one antigenic marker and wherein said marker, when presented in the context of the retrovirus-like particle, is capable of generating an immune response specific to said antigenic marker when the particle is administered to a host.

2. The virus-like particle of claim 1, wherein said at least one antigenic marker is inserted into an insertion site located between amino acid residues 210 and 211 of the gag gene product of the HIV-1 isolate LAI or the corresponding location of other retroviral gag gene products.

3. The virus-like particle of claim 2, wherein said at least one antigenic marker comprises from 1 to 4 tandem copies of the amino acid sequence AFDTRNRIIEVEN (SEQ ID:1).

4. A non-infectious, immunogenic, non-replicating human immunodeficiency virus (HIV)-like particle containing a plurality of mutations of the viral genome resulting in a virus-like particle comprising the following:

(1) a modified Gag protein, wherein said protein contains a modification, in the first Cys-His box only, wherein at least one amino acid residue has been replaced in said first Cys-His box, said replacement resulting in a reduction of gag-dependent genomic viral RNA packaging in the virus-like particle while retaining the immunogenicity of said virus-like particle;

(2) a deficient reverse transcriptase, wherein said deficiency results from a deletion of that portion of the pol gene responsible for reverse transcriptase activity, said deletion substantially eliminating reverse transcriptase activity in the virus-like particle;

(3) a deficient integrase, wherein said deficiency results from a deletion of that portion of the pol gene responsible for integrase activity, said deletion substantially eliminating integrase activity in the virus-like particle; and (4) a deficient RNase H, wherein the deficiency results from a deletion of that portion of the pol gene responsible for RNase H activity, said deletion substantially eliminating RNase H activity in the virus-like particle;

wherein said particle is encoded by a modified HIV genome devoid of long terminal repeats (LTRs) and containing the gag, pol and env genes in their natural genomic arrangement, and said virus-like particle further comprising a modified env gene product comprising a non-retroviral heterologous antigenic anchor sequence, wherein said heterologous anchor sequence replaces the endogenous anchoring functions of the env gene product wherein said particle is encoded by said modified HIV genome deficient in long terminal repeats is further modified by a heterologous nucleic acid insert encoding said heterologous antigenic anchor sequence and wherein said sequence, when generated in the context of the retrovirus-like particle, is capable of generating an immune response specific to said antigenic anchor sequence when the particle is administered to a host.

5. The virus-like particle of claim 4, wherein said anchor sequence is inserted into an insertion site of the env gene product adjacent to and upstream of functional cleavage sites of the env gene product.

6. The virus-like particle of claim 5, wherein said insertion site is located between amino acid residues 507 and 508 of the env gene product of the HIV-1 isolate LAI or the corresponding location of other retroviral env gene products.

7. The virus-like particle of claim 6, wherein the anchor sequence includes an amino acid sequence WILWISFAISCFLLCVVCWGSSCGPAKKATLGAT FAFDSKEEWCREKKEQWE (SEQ ID NO:4).

8. The virus-like particle of claim 6, wherein the anchor sequence includes an amino acid sequence WILWISFAISCFLLCVVLLGFIMW (SEQ ID NO:2).

9. The virus-like particle of claim 6, wherein the anchor sequence includes an amino acid sequence STVASSLALAIMIAGLSFWMCSNGSLQ (SED ID NO:3).

10. The virus-like particle of claim 1, wherein the human immunodeficiency virus is selected from the group consisting of HIV-1 and HIV-2.

11. An immunogenic composition capable of eliciting a retroviral specific immune response, comprising the virus-like particle of claim 1 or 4, and a carrier therefor.

12. The immunogenic composition of claim 11 formulated for mucosal or parenteral administration.

13. The immunogenic composition of claim 11 formulated for oral, anal, vaginal, or intranasal administration.

14. The immunogenic composition of claim 11 further comprising at least one other immunogenic and/or immunostimulating material.

15. The immunogenic composition of claim 14, wherein the at least one other immunostimulating material is an adjuvant.

16. The composition of claim 15, wherein the adjuvant is aluminum phosphate, aluminum hydroxide, Freund's incomplete adjuvant, or QS21.

17. The virus-like of claim 4 wherein the at least one amino acid is contained within amino acids $Cys^{392}$ to Cys 395 of the gag gene product of the HIV-1 isolate LAI or the corresponding region of other HIV retroviral gag gene products.

18. The virus-like particles of claim 17 wherein $Cys^{392}$ and/or $Cys^{395}$ is replaced by serine.

19. The virus-like particles of claim 18 wherein both $Cys^{392}$ and $Cys^{395}$ are replaced by serine.

20. The virus-like particles of claim 4 wherein the at least a portion of the pol gene product contributing to reverse transcriptase activity is contained between amino acids $Pro^{168}$ and $Leu^{727}$ of the pot gene product of the HIV-1 isolate LAI or the corresponding region of other HIV retroviral pol gene products.

21. The virus-like particles of claim 4 wherein the at least a portion of the pol gene product contributing to integrase activity is contained between amino acids $Phe^{728}$ and $Asp^{1016}$ of the pol gene product of the HIV-1 isolate LAI or the corresponding region of other HIV retroviral pol gene products.

22. The virus-like particles of claim 4 wherein the substantial elimination of reverse transcriptase activity, integrase activity and RNase H activity all are substantially eliminated by deleting a portion of the pol gene product corresponding to amino acids $Pro^{192}$ to $Trp^{835}$ of the HIV-1 isolate LAI or the corresponding region of other HIV retroviral pol gene products.

23. The virus-like particles of claim 4 wherein the human immunodeficiency virus is selected from the group consisting of HIV-1 and HIV-2.

24. The virus-like particle of claim 1, wherein the at least one amino acid is contained within amino acids Cys392 to Cys395 of the gag gene product of the HIV-1 isolate LAI or the corresponding region of other HIV retroviral gag gene products.

25. The virus-like particle of claim 24, wherein $Cys^{392}$ and/or $Cys^{395}$ is replaced by serine.

26. The virus-like particle of claim 25, wherein both $Cys^{392}$ and $Cys^{395}$ are replaced by serine.

27. The virus-like particle of claim 1, wherein the at least a portion of the pol gene product contributing to reverse transcriptase activity is contained between amino acids $Pro^{168}$ and $Leu^{727}$ of the pot gene product of the HIV-1 isolate LAI or the corresponding region of other HIV retroviral pol gene products.

28. The virus-like particle of claim 1, wherein the at least a portion of the pol gene product contributing to integrase activity is contained between amino acids $Phe^{728}$ and $Asp^{1016}$ of the pol gene product of the HIV-1 isolate LAI or the corresponding region of other HIV retroviral pol gene products.

29. The virus-like particle of claim 1, wherein the substantial elimination of reverse transcriptase activity, integrase activity and RNase H activity all are substantially eliminated by deleting a portion of the pol gene product corresponding to amino acids $Pro^{192}$ to $Trp^{835}$ of the HIV-1 isolate LAI or the corresponding region of other HIV retroviral pol gene products.

* * * * *

SEQUENCE LISTING

```
(1) GENERAL INFORMATION:

   (iii) NUMBER OF SEQUENCES: 26


(2) INFORMATION FOR SEQ ID NO:1:

     (i) SEQUENCE CHARACTERISTICS:
          (A) LENGTH: 13 amino acids
          (B) TYPE: amino acid
          (C) STRANDEDNESS: single
          (D) TOPOLOGY: linear

    (xi) SEQUENCE DESCRIPTION: SEQ ID NO:1:

Ala Phe Asp Thr Arg Asn Arg Ile Ile Glu Val Glu Asn
1               5                   10


(2) INFORMATION FOR SEQ ID NO:2:

     (i) SEQUENCE CHARACTERISTICS:
          (A) LENGTH: 24 amino acids
          (B) TYPE: amino acid
          (C) STRANDEDNESS: single
          (D) TOPOLOGY: linear

    (xi) SEQUENCE DESCRIPTION: SEQ ID NO:2:

Trp Ile Leu Trp Ile Ser Phe Ala Ile Ser Cys Phe Leu Leu Cys Val
1               5                   10                  15

Val Leu Leu Gly Phe Ile Met Trp
            20


(2) INFORMATION FOR SEQ ID NO:3:

     (i) SEQUENCE CHARACTERISTICS:
```

-continued (A) LENGTH: 27 amino acids
(B) TYPE: amino acid
(C) STRANDEDNESS: single
(D) TOPOLOGY: linear (xi) SEQUENCE DESCRIPTION: SEQ ID NO:3:

```
Ser Thr Val Ala Ser Ser Leu Ala Leu Ala Ile Met Ile Ala Gly Leu
1               5                   10                  15

Ser Phe Trp Met Cys Ser Asn Gly Ser Leu Gln
            20                  25
```

(2) INFORMATION FOR SEQ ID NO:4:

(i) SEQUENCE CHARACTERISTICS:
(A) LENGTH: 52 amino acids
(B) TYPE: amino acid
(C) STRANDEDNESS: single
(D) TOPOLOGY: linear (xi) SEQUENCE DESCRIPTION: SEQ ID NO:4:

```
Trp Ile Leu Trp Ile Ser Phe Ala Ile Ser Cys Phe Leu Leu Cys Val
1               5                   10                  15

Val Cys Trp Gly Ser Ser Cys Gly Pro Ala Lys Lys Ala Thr Leu Gly
            20                  25                  30

Ala Thr Phe Ala Phe Asp Ser Lys Glu Glu Trp Cys Arg Glu Lys Lys
        35                  40                  45

Glu Gln Trp Glu
    50
```

(2) INFORMATION FOR SEQ ID NO:5:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:5:

```
GCATTCGACA CTAGAAATAG AATAATAGAA GTTGAAAAT                            39
```

(2) INFORMATION FOR SEQ ID NO:6:

(i) SEQUENCE CHARACTERISTICS:
(A) LENGTH: 39 base pairs
(B) TYPE: nucleic acid
(C) STRANDEDNESS: single
(D) TOPOLOGY: linear (xi) SEQUENCE DESCRIPTION: SEQ ID NO:6:

```
CGTAAGCTGT GATCTTTATC TTATTATCTT CAACTTTTA                            39
```

(2) INFORMATION FOR SEQ ID NO:7:

(i) SEQUENCE CHARACTERISTICS:
(A) LENGTH: 71 base pairs
(B) TYPE: nucleic acid
(C) STRANDEDNESS: single
(D) TOPOLOGY: linear (xi) SEQUENCE DESCRIPTION: SEQ ID NO:7:

```
TGGATCCTGT GGATTCCTTT GCCATATCAT GCTTTTTGCT TTGTGTTGTT TTGCTGGGGT     60

TCATCATGTG G                                                          71
```

(2) INFORMATION FOR SEQ ID NO:8:

-continued (i) SEQUENCE CHARACTERISTICS:
(A) LENGTH: 72 base pairs
(B) TYPE: nucleic acid
(C) STRANDEDNESS: single
(D) TOPOLOGY: linear (xi) SEQUENCE DESCRIPTION: SEQ ID NO:8:

ACCTAGGACA CCTAAAGGAA ACGGTATAGT ACGAAAAACG AAACACAACA AAACGACCCC 60

AAGTAGTACA CC 72

(2) INFORMATION FOR SEQ ID NO:9:

(i) SEQUENCE CHARACTERISTICS:
(A) LENGTH: 81 base pairs
(B) TYPE: nucleic acid
(C) STRANDEDNESS: single
(D) TOPOLOGY: linear (xi) SEQUENCE DESCRIPTION: SEQ ID NO:9:

TCAACAGTGG CAAGTTCCCT AGCACTGGCA ATCATGATAG CTGGTCTATC TTTTTGGATG 60

TGTTCCAATG GGTCATTGCA G 81

(2) INFORMATION FOR SEQ ID NO:10:

(i) SEQUENCE CHARACTERISTICS:
(A) LENGTH: 81 base pairs
(B) TYPE: nucleic acid
(C) STRANDEDNESS: single
(D) TOPOLOGY: linear (xi) SEQUENCE DESCRIPTION: SEQ ID NO:10:

AGTTGTCACC GTTCAAGGGA TCGTGACCGT TAGTACTATC GACCAGATAG AAAAACCTAC 60

ACAAGGTTAC CCAGTAACGT C 81

(2) INFORMATION FOR SEQ ID NO:11:

(i) SEQUENCE CHARACTERISTICS:
(A) LENGTH: 156 base pairs
(B) TYPE: nucleic acid
(C) STRANDEDNESS: single
(D) TOPOLOGY: linear (xi) SEQUENCE DESCRIPTION: SEQ ID NO:11:

TGGATCCTGT GGATTTCCTT TGCCATATCA TGCTTTTTGC TTTGTGTTGT TTGCTGGGGT 60

TCATCATGTG GGCCTGCCAA AAAGGCAACA TTAGGTGCAA CATTTGCATT TGATAGTAAA 120

GAAGAGTGGT GCAGAGAGAA AAAAGAGCAG TGGGAA 156

(2) INFORMATION FOR SEQ ID NO:12:

(i) SEQUENCE CHARACTERISTICS:
(A) LENGTH: 156 base pairs
(B) TYPE: nucleic acid
(C) STRANDEDNESS: single
(D) TOPOLOGY: linear (xi) SEQUENCE DESCRIPTION: SEQ ID NO:12:

ACCTAGGACA CCTAAAGGAA ACGGTATAGT ACGAAAAACG AAACACAACA AACGACCCCA 60

AGTAGTACAC CCGGACGGTT TTTCCGTTGT AATCCACGTT GTAAACGTAA ACTATCATTT 120

CTTCTCACCA CGTCTCTCTT TTTTCTCGTC ACCCTT 156

(2) INFORMATION FOR SEQ ID NO:13:

-continued (i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:13:

TGTTTCAATT GT 12

(2) INFORMATION FOR SEQ ID NO:14:

(i) SEQUENCE CHARACTERISTICS:
(A) LENGTH: 12 base pairs
(B) TYPE: nucleic acid
(C) STRANDEDNESS: single
(D) TOPOLOGY: linear (xi) SEQUENCE DESCRIPTION: SEQ ID NO:14:

AGTTTCAATA GT 12

(2) INFORMATION FOR SEQ ID NO:15:

(i) SEQUENCE CHARACTERISTICS:
(A) LENGTH: 63 base pairs
(B) TYPE: nucleic acid
(C) STRANDEDNESS: single
(D) TOPOLOGY: linear (xi) SEQUENCE DESCRIPTION: SEQ ID NO:15:

GGACTAGTAC CCTTCAGGAA CAAATAGGAT GGATGACAAA TAATCCACCT ATCCCAGTAG 60

GAG 63

(2) INFORMATION FOR SEQ ID NO:16:

(i) SEQUENCE CHARACTERISTICS:
(A) LENGTH: 62 base pairs
(B) TYPE: nucleic acid
(C) STRANDEDNESS: single
(D) TOPOLOGY: linear (xi) SEQUENCE DESCRIPTION: SEQ ID NO:16:

CTCGGGCCCT GCAATTTCTG GCTATGTGCC CTTCTTTGCC ACTATTGAAA CTCTTAACAA 60

TC 62

(2) INFORMATION FOR SEQ ID NO:17:

(i) SEQUENCE CHARACTERISTICS:
(A) LENGTH: 23 base pairs
(B) TYPE: nucleic acid
(C) STRANDEDNESS: single
(D) TOPOLOGY: linear (xi) SEQUENCE DESCRIPTION: SEQ ID NO:17:

GTATAAGTGA GTAGCGGCCG CAC 23

(2) INFORMATION FOR SEQ ID NO:18:

(i) SEQUENCE CHARACTERISTICS:
(A) LENGTH: 6 base pairs
(B) TYPE: nucleic acid
(C) STRANDEDNESS: single
(D) TOPOLOGY: linear (xi) SEQUENCE DESCRIPTION: SEQ ID NO:18:

ATCATT 6

-continued (2) INFORMATION FOR SEQ ID NO:19:

(i) SEQUENCE CHARACTERISTICS:
(A) LENGTH: 48 base pairs
(B) TYPE: nucleic acid
(C) STRANDEDNESS: single
(D) TOPOLOGY: linear (xi) SEQUENCE DESCRIPTION: SEQ ID NO:19:

GGTGCATTCG ACACTAGAAA TAGAATAATA GAAGTTGAAA ATGGTGCA 48

(2) INFORMATION FOR SEQ ID NO:20:

(i) SEQUENCE CHARACTERISTICS:
(A) LENGTH: 48 base pairs
(B) TYPE: nucleic acid
(C) STRANDEDNESS: single
(D) TOPOLOGY: linear (xi) SEQUENCE DESCRIPTION: SEQ ID NO:20:

ACGTCCACGT AAGCTGTGAT CTTTATCTTA TTATCTTCAA CTTTTACC 48

(2) INFORMATION FOR SEQ ID NO:21:

(i) SEQUENCE CHARACTERISTICS:
(A) LENGTH: 16 amino acids
(B) TYPE: amino acid
(C) STRANDEDNESS: single
(D) TOPOLOGY: linear (xi) SEQUENCE DESCRIPTION: SEQ ID NO:21:

```
Gly Ala Phe Asp Thr Arg Asn Arg Ile Ile Glu Val Glu Asn Gly Ala
1               5                   10                  15
```

(2) INFORMATION FOR SEQ ID NO:22:

(i) SEQUENCE CHARACTERISTICS:
(A) LENGTH: 29 amino acids
(B) TYPE: amino acid
(C) STRANDEDNESS: single
(D) TOPOLOGY: linear (xi) SEQUENCE DESCRIPTION: SEQ ID NO:22:

```
Gly Pro Ala Lys Lys Ala Thr Leu Gly Ala Thr Phe Ala Phe Asp Ser
1               5                   10                  15

Lys Glu Glu Trp Cys Arg Glu Lys Lys Glu Gln Trp Glu
            20                  25
```

(2) INFORMATION FOR SEQ ID NO:23:

(i) SEQUENCE CHARACTERISTICS:
(A) LENGTH: 19 amino acids
(B) TYPE: amino acid
(C) STRANDEDNESS: single
(D) TOPOLOGY: linear (xi) SEQUENCE DESCRIPTION: SEQ ID NO:23:

```
Asn Lys Arg Lys Arg Ile His Ile Gly Pro Gly Arg Ala Phe Tyr Thr
1               5                   10                  15

Thr Lys Asn
```

(2) INFORMATION FOR SEQ ID NO:24:

(i) SEQUENCE CHARACTERISTICS:
(A) LENGTH: 19 amino acids

-continued

```
          (B) TYPE: amino acid
          (C) STRANDEDNESS: single
          (D) TOPOLOGY: linear

    (xi) SEQUENCE DESCRIPTION: SEQ ID NO:24:

Asn Thr Arg Lys Ser Ile Tyr Ile Gly Pro Gly Arg Ala Phe His Thr
1               5                   10                  15

Thr Gly Arg


(2) INFORMATION FOR SEQ ID NO:25:

     (i) SEQUENCE CHARACTERISTICS:
          (A) LENGTH: 21 amino acids
          (B) TYPE: amino acid
          (C) STRANDEDNESS: single
          (D) TOPOLOGY: linear

    (xi) SEQUENCE DESCRIPTION: SEQ ID NO:25:

Asn Thr Arg Lys Arg Ile Arg Ile Gln Arg Gly Pro Gly Arg Ala Phe
1               5                   10                  15

Val Thr Ile Gly Lys
            20


(2) INFORMATION FOR SEQ ID NO:26:

     (i) SEQUENCE CHARACTERISTICS:
          (A) LENGTH: 37 amino acids
          (B) TYPE: amino acid
          (C) STRANDEDNESS: single
          (D) TOPOLOGY: linear

    (xi) SEQUENCE DESCRIPTION: SEQ ID NO:26:

Met Lys Lys Thr Arg Phe Val Leu Asn Ser Ile Ala Leu Gly Leu Ser
1               5                   10                  15

Val Leu Ser Thr Ser Phe Val Ala Gln Ala Thr Leu Pro Ser Phe Val
            20                  25                  30

Ser Glu Gln Asn Ser
        35
```